United States Patent
Simon et al.

(10) Patent No.: US 9,052,319 B2
(45) Date of Patent: Jun. 9, 2015

(54) METHOD OF GUIDING PROSTATE BIOPSY LOCATION

(75) Inventors: Avi Simon, Rehovot (IL); Meir Weksler, Mazkeret Batia (IL); Amos Breskin, Nes Ziona (IL); Rachel Chechik, Moshav Beit Hanan (IL); Marco Cortesi, Varedllino (IT)

(73) Assignee: ProSight Ltd., Mazkeret Batia (IL)

( * ) Notice: Subject to any disclaimer, the term of this patent is extended or adjusted under 35 U.S.C. 154(b) by 326 days.

(21) Appl. No.: 13/512,929

(22) PCT Filed: Dec. 10, 2009

(86) PCT No.: PCT/IL2009/001172
§ 371 (c)(1),
(2), (4) Date: May 31, 2012

(87) PCT Pub. No.: WO2010/067364
PCT Pub. Date: Jun. 17, 2010

(65) Prior Publication Data
US 2012/0282648 A1 Nov. 8, 2012

Related U.S. Application Data

(60) Provisional application No. 61/121,201, filed on Dec. 10, 2008.

(51) Int. Cl.
*G01N 33/574* (2006.01)
(52) U.S. Cl.
CPC ................................. *G01N 33/57434* (2013.01)
(58) Field of Classification Search
USPC .......................................... 435/4, 6.14, 7.23
See application file for complete search history.

(56) References Cited

U.S. PATENT DOCUMENTS

| 2004/0092807 A1* | 5/2004 | Breskin et al. ................ 600/407 |
| 2004/0229300 A1* | 11/2004 | Frederickson ............... 435/7.23 |
| 2006/0193781 A1* | 8/2006 | Frederickson et al. ...... 424/9.36 |
| 2010/0312072 A1* | 12/2010 | Breskin et al. ................ 600/300 |

FOREIGN PATENT DOCUMENTS

WO WO 2010/067364 6/2010

OTHER PUBLICATIONS

International Preliminary Report on Patentability Dated Jun. 23, 2011 From the International Bureau of WIPO Re. Application No. PCT/IL2009/001172.
International Search Report and the Written Opinion Dated Mar. 16, 2010 From the International Searching Authority Re. Application No. PCT/IL2009/001172.
Cortesi et al. "Clinical Assessment of the Cancer Diagnostic Value of Prostatic Zinc: A Comprehensive Needle-Biopsy Study", The Prostate, XP009130496, 68(9): 994-1006, Jun. 15, 2008.
Shilstein et al. "Prostatic Zn Determination for Prostate Cancer Diagnosis", Talanta, XP025001074, 70(5): 914-921, Dec. 15, 2006.
Vartsky et al. "Prostatic Zinc and Prostate Specific Antigen: An Experimental Evaluation of Their Combined Diagnostic Value", The Journal of Urology, XP005543110, 170(6): 2258-2262, Dec. 1, 2003.
Zaichick et al. "Zinc in the Human Prostate Gland: Normal, Hyperplastic and Cancerous", International Urology and Nephrology, XP008001184, 29(5): 565-574, Jan. 1, 1997.

* cited by examiner

*Primary Examiner* — Ralph Gitomer

(57) ABSTRACT

A method of analyzing a plurality of biopsy cores extracted from a plurality of respective biopsy locations in a prostate is disclosed. The method comprises: measuring a level of a chemical element in each of the biopsy cores, and generating a chemical element map of at least a portion of the prostate based on the levels and the respective biopsy locations. In some embodiments, the method determines at least one additional biopsy location for a future biopsy in the prostate.

12 Claims, 31 Drawing Sheets

Cancer Area $LC_{Zn}$ = 25 ppm

METHOD OF GUIDING PROSTATE BIOPSY LOCATION

RELATED APPLICATION

This application is a National Phase of PCT Patent Application No. PCT/IL2009/001172 having International filing date of Dec. 10, 2009, which claims the benefit of priority of U.S. Provisional Patent Application No. 61/121,201, filed Dec. 10, 2008. The contents of the above applications are incorporated herein by reference.

FIELD AND BACKGROUND OF THE INVENTION

The present invention, in some embodiments thereof, relates to analysis of biopsy cores, and, more particularly, but not exclusively, to a method and system for automatically analyzing biopsy cores extracted from a plurality of respective biopsy locations in a prostate.

Based on recent statistics, for the general population, a man has about a 17 percent chance (1 in 6) of being diagnosed with prostate cancer at some point during his lifetime (lifetime risk), and a 3 percent chance (1 in 33) of dying from prostate cancer.

Current screening methods for symptomatic prostate-cancer (PCa) detection, such as digital rectal examination (DRE), transrectal ultrasound (TRUS) or prostate specific antigen blood test (PSA), lack sensitivity and specificity. For example, elevations in PSA occur not only in cancer cases but also in some non-neoplastic conditions, such as nodular hyperplasia (approx 25% PSA>4 ng/ml) and prostatitis, leading to a considerable overlap in levels of serum PSA between that found in such conditions and that found in prostate cancer patients (approx 80% PSA>4 ng/ml). If suspicious findings are present in any of these screening tests, a trans-rectal ultrasound guided needle-biopsy examination (TRNB) is practiced [American College of Physicians 1997]. The rate of negative (non-cancerous) findings for TRNB examination is about 75%, which indicates a high over-prescription of this highly invasive and costly examination. Furthermore, none of the above screening methods provide information on tumor differentiation and/or location and/or dimensions. The lack of location information, which could serve as guidance during the needle-biopsy examination, leads to high false-negative rates in TRNB (of ~28% in the first examination and ~17% in repeated ones).

Clearly, an improved method for screening, imaging and staging of prostate cancer, providing reliable information on the lesion's extension and site, as well as on its pathological stage, is required for the purpose of diagnosis as well as disease management (choice, monitoring and control of therapy). Numerous improvements of standard TRUS have been developed, such as the power Doppler imaging (DPI), the colour Doppler TRUS (CDUS) and the 3 dimensional Doppler (3DD). However, these modalities can not reliably provide information about the pathological stage of the lesions. Methodologies based on endo-rectal magnetic resonance imaging (ER-MRI) also exist but they are expensive and their use is limited to pre-operative staging.

Methods and devices for detection, localization and histological grading of PCa have been proposed (see PCT WO 2004/041060 to Breskin et al, filed Nov. 6, 2003), based on mapping the zinc concentration distribution within the prostate. The proposed non-invasive method consists of local x-ray irradiation of the gland, followed by the measurement of characteristic zinc emission with a trans-rectal X-Ray Fluorescence (XRF) probe.

Additional background art includes Zaichick et al., International Urology and Nephrology 28(5), 687-694, 1996; Zaichick et al., International Urology and Nephrology 29(5), 565-574, 1997; Habib et al., Br. J. Cancer 39 700-704, 1979; Costello et al., J. Inorg. Biochem. 78 161-165, 2000; Lahtonen R, The Prostate 6 177-183, 1985; Shilstein et al., J. Phys. Med. Biol. 49 1-15, 2004; Shilstein et al., Talanta 70 914-921, 2006; and Vartsky et al., J. Urol. 170 2258-2262, 2003.

SUMMARY OF THE INVENTION

According to an aspect of some embodiments of the present invention there is provided a method of analyzing a plurality of biopsy cores extracted from a plurality of respective biopsy locations in a prostate. The method comprises: measuring a level of a chemical element in each of the biopsy cores, and generating a chemical element map of at least a portion of the prostate based on the levels and the respective biopsy locations. In various exemplary embodiments of the invention the method calculates a gradient of the chemical element over the map, and uses the gradient for determining at least one additional biopsy location for a future biopsy in the prostate.

According to some embodiments of the invention the method further comprises adding to the plurality of biopsy cores at least one additional biopsy core from the prostate at the at least one additional biopsy location, thereby updating the plurality of biopsy cores, measuring a level of the chemical element in the at least one additional biopsy core, and repeating the calculation and the determination for the updated plurality of biopsy cores.

According to an aspect of some embodiments of the present invention there is provided a method of guiding a biopsy device in a prostate. The method comprises: extracting a plurality of biopsy cores from a plurality of respective biopsy locations in a prostate, executing a biopsy analysis method such as the method described above or exemplified hereinunder, receiving from the biopsy analysis method at least one additional biopsy location, and extracting at least one biopsy core from the additional biopsy location(s). According to some embodiments of the invention the method iteratively repeats the analysis and extraction of additional biopsy cores.

According to some embodiments of the invention the method further comprises displaying at least one of: the plurality of respective biopsy locations, the chemical element map, and the at least one additional biopsy location on an image of the prostate.

According to some embodiments of the invention the method further comprises estimating a location of a tumor in the prostate.

According to some embodiments of the invention the method further comprises estimating a size of the tumor.

According to some embodiments of the invention the additional biopsy location(s) comprise a plurality of additional biopsy locations at the tumor.

According to some embodiments of the invention the additional biopsy location(s) comprises at least one additional biopsy location nearby the tumor.

According to some embodiments of the invention the method further comprises removing the biopsy cores from biopsy devices to a core holder prior to the measurement. In various exemplary embodiments of the invention the removal is done automatically.

According to some embodiments of the invention the method further comprises estimating a grade of a prostate cancer from the chemical element map.

According to some embodiments of the invention the estimation of the grade comprises: clustering the chemical element map according to levels of the chemical element at the respective locations; and estimating the cancer grade of at least one tissue region, based, at least in part, on levels of the chemical element associated with a cluster representing the tissue region.

According to some embodiments of the invention the method further comprises segmenting the chemical element data into a plurality of segments, each corresponding to a predetermined range of levels of the chemical element, wherein the clustering is according to the segments.

According to some embodiments of the invention the method further comprises determining a location of a tumor in the prostate based on the at least one cluster.

According to some embodiments of the invention the method further comprises estimating a cancer stage of the tissue region.

According to an aspect of some embodiments of the present invention there is provided a system for analyzing a plurality of biopsy cores extracted from a plurality of respective biopsy locations in a prostate. The system comprises: a processing system; a stage, for holding the biopsy cores in addressable locations on the stage, wherein the addressable locations respectively correspond to the biopsy locations; and an irradiation-detection system, configured for irradiating the addressable locations by a beam of exciting radiation, detecting fluorescent x-ray radiation emitted from chemical element in the respective biopsy cores and transmitting chemical element data to the processing system responsively to the detected radiation.

In various exemplary embodiments of the invention at least one of the stage and the irradiation-detection system is movable. In these embodiments, the system preferably comprises a controller, for controlling relative motion between the stage and the irradiation-detection system such that the beam scans the stage and for transmitting core identification data to the processing system synchronously with the scan.

According to some embodiments of the invention the processing system is configured for receiving the biopsy locations generating a chemical element map of at least a portion of the prostate based on combined information including the chemical element data, the core identification data and the biopsy locations.

According to some embodiments of the invention the processing system is configured for calculating a gradient of the chemical element over the map, and determining, based on the gradient, at least one additional biopsy location for a future biopsy in the prostate.

According to some embodiments of the invention the processing system is configured for controlling a display device to display at least one of: the plurality of respective biopsy locations, the chemical element map, and the at least one additional biopsy location on an image of the prostate. According to some embodiments of the invention the processing system comprises the display device.

According to some embodiments of the invention the processing system is configured for estimating a location of a tumor in the prostate.

According to some embodiments of the invention the processing system is configured for estimating a size of the tumor.

According to some embodiments of the invention the processing system is configured for estimating a grade of a prostate cancer from the chemical element map.

According to some embodiments of the invention each core is positioned on the stage within a core holder, wherein the system further comprises a mechanism from automatically removing the core from a biopsy device to the core holder.

According to some embodiments of the invention the processing system comprises: a clustering module, configured for clustering the chemical element map according to according to levels of the chemical element at the respective locations; and a grade estimating module, configured for estimating a cancer grade of at least one tissue region, based, at least in part, on levels of the chemical element associated with a cluster representing the tissue region.

According to some embodiments of the invention the processing system further comprises a segmentation module configured for segmenting the chemical element data into a plurality of segments, each corresponding to a predetermined range of levels of the chemical element, wherein the module is configured for clustering the map according to the segments.

According to some embodiments of the invention the processing system further comprises a staging module, for estimating a cancer stage of the tissue region.

According to some embodiments of the invention the cluster(s) comprises a cluster corresponding to a lowest range of zinc levels in the zinc data.

According to some embodiments of the invention the cluster(s) comprises a cluster corresponding to a next-to-lowest range of zinc levels in the zinc data.

According to some embodiments of the invention the segmentation and the clustering is effected by expectation-maximization technique.

According to some embodiments of the invention the estimation of the cancer grade is based on a predetermined dependence of the cancer grade on: (i) a size of the cluster and (ii) chemical element levels associated with the cluster.

According to some embodiments of the invention the cancer grade is selected from a predetermined set of cancer grades, and wherein the predetermined dependence is expressed as a plurality of predictive loci in a two-dimensional plane spanned by a chemical element level axis and a cluster size axis, one locus for each cancer grade in the set.

According to some embodiments of the invention an average chemical element level of the cluster is classified according to a plurality of predetermined chemical element level thresholds and a size of the cluster is classified according to a plurality of cluster size thresholds, and wherein the cancer grade is estimated based on both the classifications.

According to some embodiments of the invention the cancer grade is scaled according to the Gleason grading scale.

According to some embodiments of the invention the chemical element is zinc.

According to some embodiments of the invention an average zinc level associated with the cluster below about 40 parts per million indicates that the cancer grade is equivalent to Gleason score 9.

According to some embodiments of the invention an average zinc level associated with the cluster below 70 parts per million indicates that the cancer grade is equivalent to a Gleason grade having a primary grade which is at least 4.

According to some embodiments of the invention an average zinc level from about 30 parts per million to about 40 parts per million indicates that the cancer grade is equivalent to Gleason grade 4+5, and an average zinc level below about 30 parts per million indicates that the cancer grade is equivalent to Gleason grade 5+4.

According to some embodiments of the invention a size of the tissue region above about 0.5 cm$^2$, and an average zinc level associated with the cluster from about 30 parts per million to about 70 parts per million indicates that the grade is equivalent to a Gleason grade having a primary grade which is 4.

According to some embodiments of the invention an average zinc level associated with the cluster from about 40 parts per million to about 55 parts per million indicates that the cancer grade is equivalent to: Gleason grade 4+5, provided that a size of the tissue region is from about 0.5 cm$^2$ to about 0.9 cm2, and Gleason grade 4+4, provided that a size of the tissue region is above 0.9 cm$^2$.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

Implementation of the method and/or system of embodiments of the invention can involve performing or completing selected tasks manually, automatically, or a combination thereof. Moreover, according to actual instrumentation and equipment of embodiments of the method and/or system of the invention, several selected tasks could be implemented by hardware, by software or by firmware or by a combination thereof using an operating system.

For example, hardware for performing selected tasks according to embodiments of the invention could be implemented as a chip or a circuit. As software, selected tasks according to embodiments of the invention could be implemented as a plurality of software instructions being executed by a computer using any suitable operating system. In an exemplary embodiment of the invention, one or more tasks according to exemplary embodiments of method and/or system as described herein are performed by a data processor, such as a computing platform for executing a plurality of instructions. Optionally, the data processor includes a volatile memory for storing instructions and/or data and/or a non-volatile storage, for example, a magnetic hard-disk and/or removable media, for storing instructions and/or data. Optionally, a network connection is provided as well. A display and/or a user input device such as a keyboard or mouse are optionally provided as well.

BRIEF DESCRIPTION OF THE DRAWINGS

Some embodiments of the invention are herein described, by way of example only, with reference to the accompanying drawings and images. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings.

DESCRIPTION OF SPECIFIC EMBODIMENTS OF THE INVENTION

Figure 1:
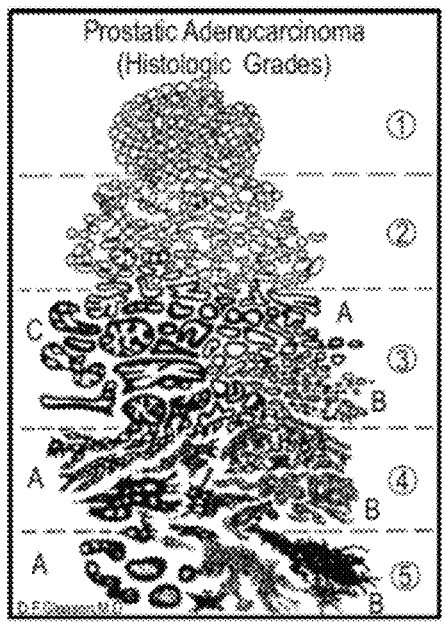
FIG. 1 describes the Gleason-grade scale for grading prostate cancer grade.

The present invention, in some embodiments thereof, relates to analysis of biopsy cores, and, more particularly, but not exclusively, to a method and system for automatically analyzing biopsy cores extracted from a plurality of respective biopsy locations in a prostate.

Before explaining at least one embodiment of the invention in detail, it is to be understood that the invention is not necessarily limited in its application to the details of construction and the arrangement of the components and/or methods set forth in the following description and/or illustrated in the drawings and/or the Examples. The invention is capable of other embodiments or of being practiced or carried out in various ways.

Some embodiments of the present invention provide means for analyzing biopsy cores extracted from a plurality of respective biopsy locations in a prostate gland of a warm-blooded male subject (animal or human). Some embodiments of the present invention provide means for detecting cancer in a subject in need of such detection. Some embodiments of the present invention provide means for estimating a grade and optionally staging the cancer of the subject. In some embodiments of the present invention the grading estimation is supplemented by a determination of an approximate location of one or more tumors in the prostate of the subject.

Some embodiments of the invention can be embodied on a tangible medium such as a computer for performing the method steps. Some embodiments of the invention can be embodied on a computer readable medium, comprising computer readable instructions for carrying out the method steps. Some embodiments of the invention can also be embodied in electronic device having digital computer capabilities arranged to run the computer program on the tangible medium or execute the instruction on a computer readable medium. Computer programs implementing method steps of the present embodiments can commonly be distributed to users on a tangible distribution medium. From the distribution medium, the computer programs can be copied to a hard disk or a similar intermediate storage medium. The computer programs can be run by loading the computer instructions either from their distribution medium or their intermediate storage medium into the execution memory of the computer, configuring the computer to act in accordance with the present embodiments. All these operations are well-known to those skilled in the art of computer systems.

Some embodiments of the present invention are useful for evaluating whether or not the subject has tumors in his prostate gland. Some embodiments are useful for evaluating the location of the tumor in his prostate gland. Some embodiments are useful for evaluating the size of the tumor in his prostate gland. Some embodiments are useful for evaluating the histological grade of the tumor in his prostate gland. Some embodiments of the present invention can be used for assessing what type of treatment is suitable for a subject having a tumor of such grade and optionally size in his prostate gland. Some embodiments of the present invention are useful for determining the efficiency of the treatment by estimating the size of a prostate cancer before and after a treatment. The present embodiments may be performed with a combination of different methods, optionally and preferably including analysis of needle-biopsy in vitro.

Generally, the cancer grade is estimated from data pertaining to the level of a chemical element at various locations within the prostate of the subject.

The data can be collected via X-ray fluorescence (XRF), as known in the art (to this end see, e.g., International Patent Publication No. WO2004/041060, the contents of which are hereby incorporated by reference). XRF is an analytical method widely used for analysis of trace elements in various matrices. Biological samples such as tissues can be analyzed intact by XRF without sample processing. In XRF, the analyzed tissue may be exposed to a given radiation dose of X-rays or low energy gamma rays from an X-ray tube or an isotopic radioactive source, which as described herein are non-limiting examples of irradiation systems and/or may form a component of such a system. This radiation causes the excitation of the atoms present in the tissue, which in turn decay by emission of characteristic fluorescent X-rays. The characteristic X-rays emitted from the sample are detected and counted by a high energy-resolution detector. The intensity of these X-rays is directly proportional to the concentration of the elements inside the tissue. In the case of zinc, the characteristic fluorescent X-ray energies are 8.6 and 9.6 keV. The sensitivity of the XRF method depends on the chemical element of interest and on the experimental conditions. The limits of detection are typically below one part per million.

Since zinc concentrations in the prostate are lower in cancerous tissue compared to normal and benign prostate hyperplasia (BPH), various exemplary embodiments of the invention zinc as the chemical element used in the analysis.

While the embodiments below are described with a particular emphasis to zinc, it is to be understood that more detailed reference to zinc is not to be interpreted as limiting the scope of the invention in any way. For example, some embodiments employ chemical elements other than zinc that are normally present in the prostate gland tissue, including, without limitation, iron, calcium or bromine. In some embodiments of the present invention detection of elements other than zinc is employed for normalization purposes. Specifically, in these embodiments zinc and at least one additional chemical element are detected, wherein the additional chemical element is used for normalization.

Figure 33:
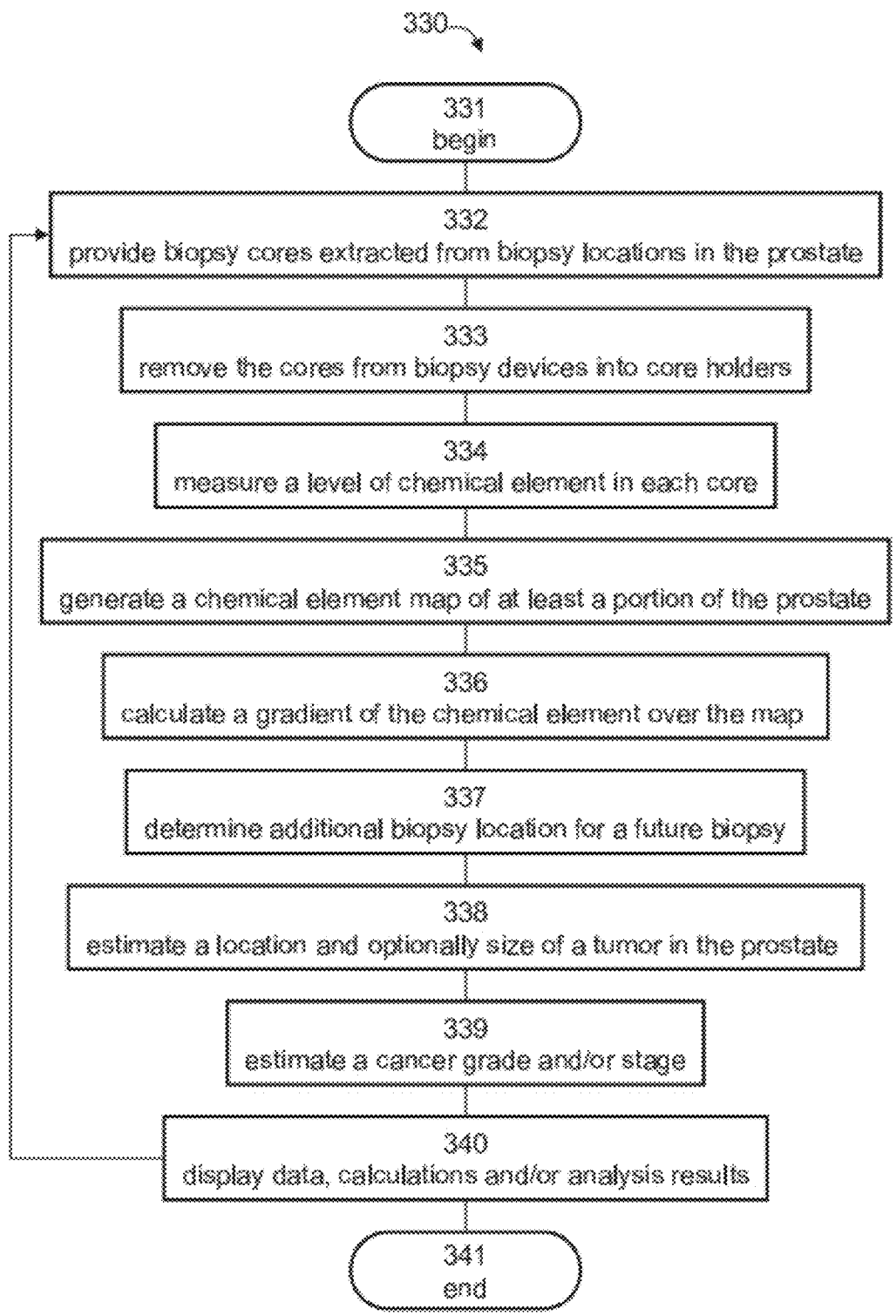
FIG. 33 is a flowchart diagram of a method suitable for analyzing a plurality of biopsy cores, according o various exemplary embodiments of the present invention.
Figure 34B:
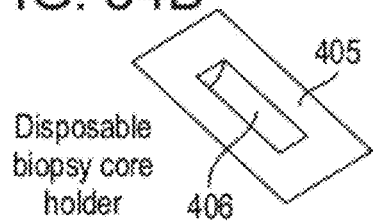
FIGS. 34A-D are schematic illustrations of a system for analyzing a plurality of biopsy cores according to various exemplary embodiments of the present invention.
Figure 34A:
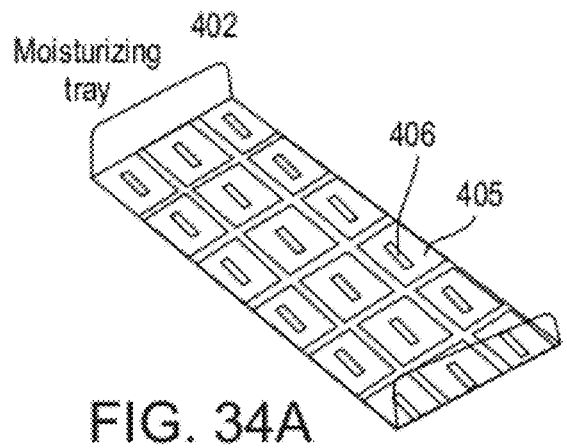
Figure 34C:
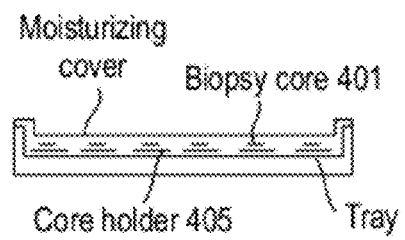
Figure 34D:
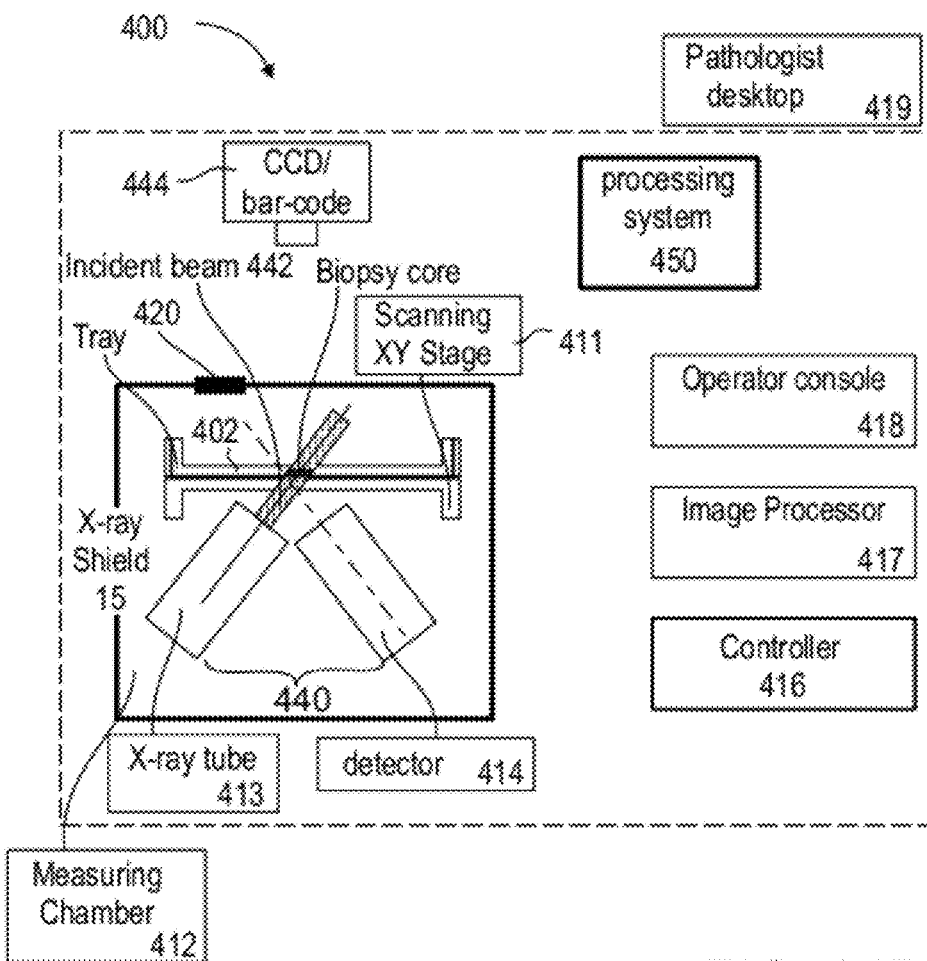

FIG. 33 is a flowchart diagram of a method 330 suitable for analyzing a plurality of biopsy cores extracted from a plurality of respective biopsy locations in a prostate, according to various exemplary embodiments of the present invention.

It is to be understood that, unless otherwise defined, the operations described hereinbelow can be executed either contemporaneously or sequentially in many combinations or orders of execution. Specifically, the ordering of the flowchart diagrams is not to be considered as limiting. For example, two or more operations, appearing in the following description or in the flowchart diagrams in a particular order, can be executed in a different order (e.g., a reverse order) or substantially contemporaneously. Additionally, several operations described below are optional and may not be executed.

Method 330 begins at 331 and continues to 332 at which a plurality of biopsy cores extracted from a plurality of respective biopsy locations in the prostate are provided. The method can extract the biopsy cores by means of a biopsy procedure (e.g., TRUS or the like), or it can receive the biopsy cores after they have been already extracted. In any event, each core is associated with a biopsy location in the prostate. The biopsy locations can be defined via fiducial marks in the prostate, for example, on an ultrasound image imported from the TRUS, or on any other image or graphical representation of the prostate.

The method can receive the biopsy cores within core holders, which are typically disposable, or on biopsy devices, e.g., disposable biopsy needles or the like. When the biopsy cores are provided on biopsy devices, the method preferably proceeds to 333 at which the biopsy cores are removed from the biopsy devices to core holders. Optionally and preferably the removal is done automatically without human intervention.

Method 330 continues to 334 at which a level of a chemical element in each of biopsy cores is measured. The chemical element, as stated, can be zinc and/or any other chemical element (iron, calcium, bromine or other) that is normally present in the prostate gland. In various exemplary embodiments of the invention the chemical element is zinc. The measurement is typically by means of x-ray fluorescence as known in the art and further detailed hereinunder. The x-ray fluorescence can also be employed for sizing the biopsy core as further detailed hereinunder.

Method 330 continues to 335 at which a chemical element map of at least a portion of the prostate is generated based on the measured levels and the biopsy locations. The map can be generated by associating to each biopsy location the level that was measured from the respective core.

The map comprises information pertaining to the content of the chemical element in the prostate gland. Since different parts of the prostate generally comprise different chemical element levels, the chemical element data in the map comprises a set of tuples, each comprising the coordinates of a region or a point in the prostate and an additional chemical element level (e.g., concentration or density of the chemical element) associated with the point or region. The chemical element data can be transformed to visible signals, in which case the map is in the form of an image.

The chemical element data are typically arranged gridwise in a plurality of picture-elements (e.g., pixels, arrangements of pixels) forming the map. Each picture-element is represented by a chemical element level over the grid. When the map is in the form of an image, each picture-element can be represented by a grey-level which corresponds to the respective chemical element level. In various exemplary embodiments of the invention the chemical element map also comprise an image of the prostate.

It is appreciated that the number of different chemical element levels can be different from the number of grey-levels. For example, an 8-bit display can generate 256 different grey-levels, but the number of different chemical element levels can, in principle, be much larger.

The term "pixel" is sometimes abbreviated herein to indicate a picture-element. However, this is not intended to limit the meaning of the term "picture-element" which refers to a unit of the composition of the chemical element map.

The terms "chemical element map", "chemical element data" and "chemical element image" are used interchangeably throughout the specification without limiting the scope of the present invention in any way. Specifically, unless otherwise defined, the use of the term "chemical element map" is not to be considered as limited to the transformation of the information regarding chemical element content in the prostate into visible signals. For example, a chemical element map can be stored in the memory of a computer readable medium as a set of tuples as described above.

Figure 17:
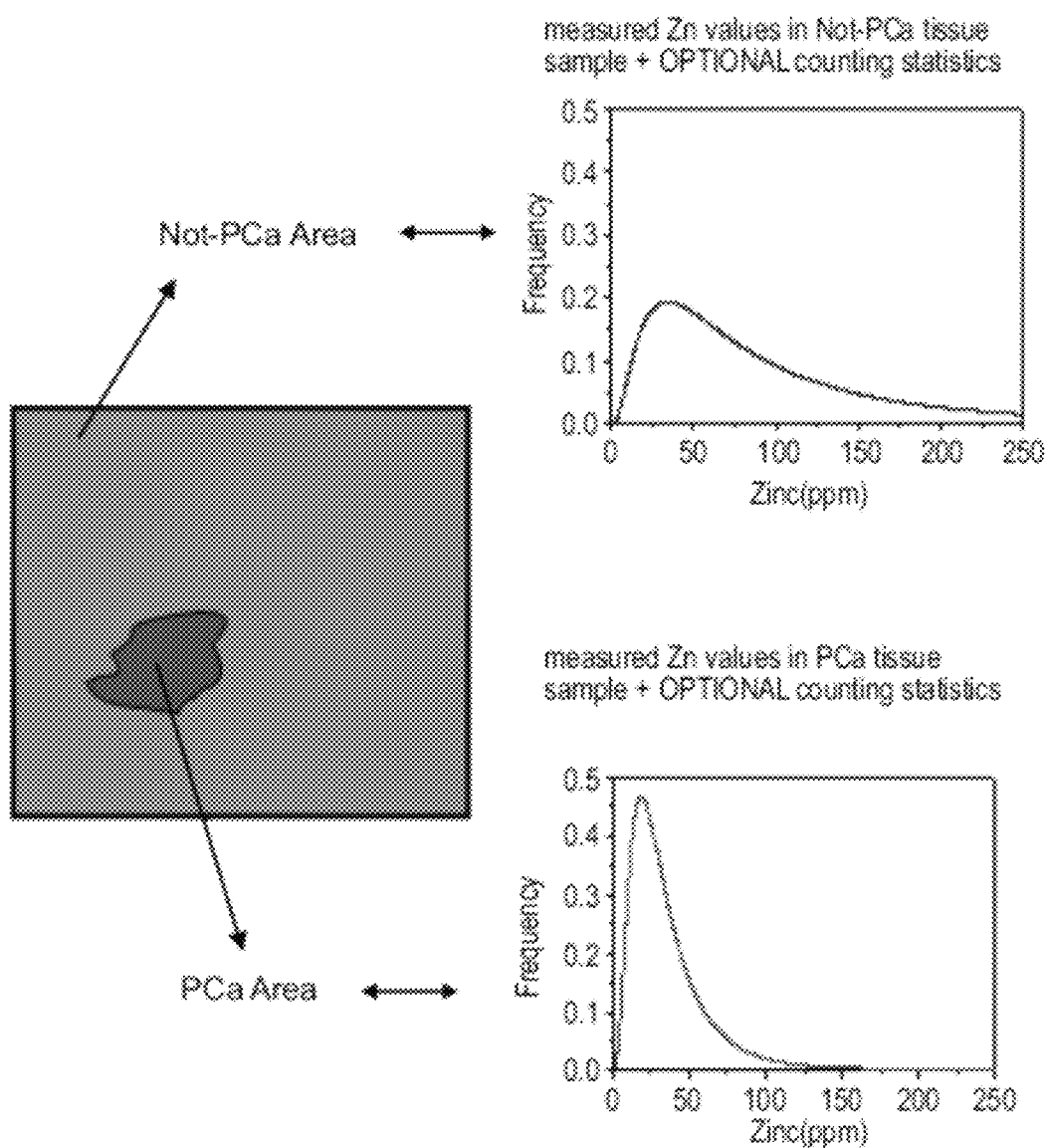
FIG. 17 shows a zinc map and corresponding frequency plots, as prepared according to various exemplary embodiments of the present invention.
Figure 22:
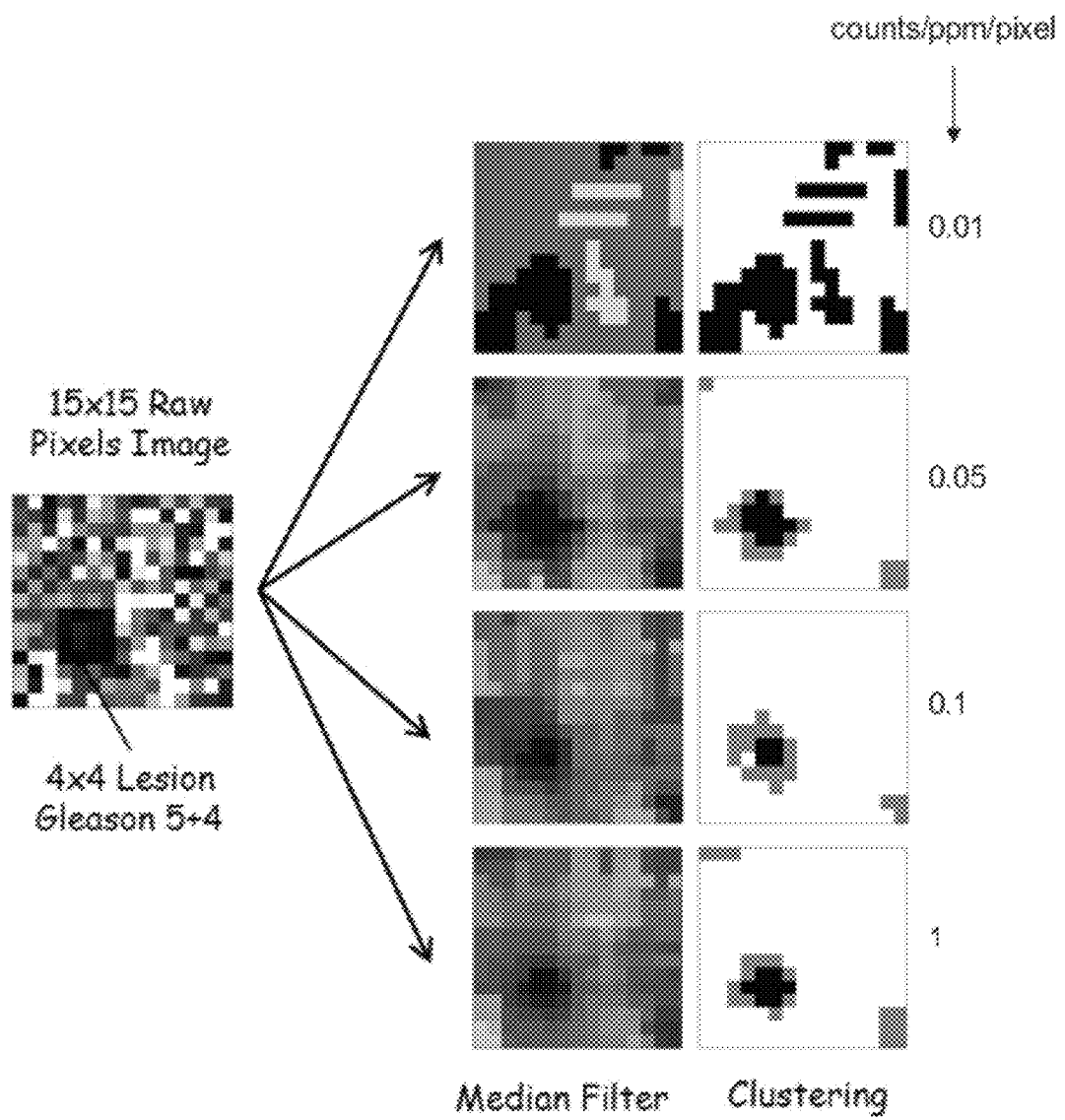
FIG. 22 is a schematic illustration representing the effects of the sensitivity on cancer area detectability, according to various exemplary embodiments of the present invention.
Figure 23:
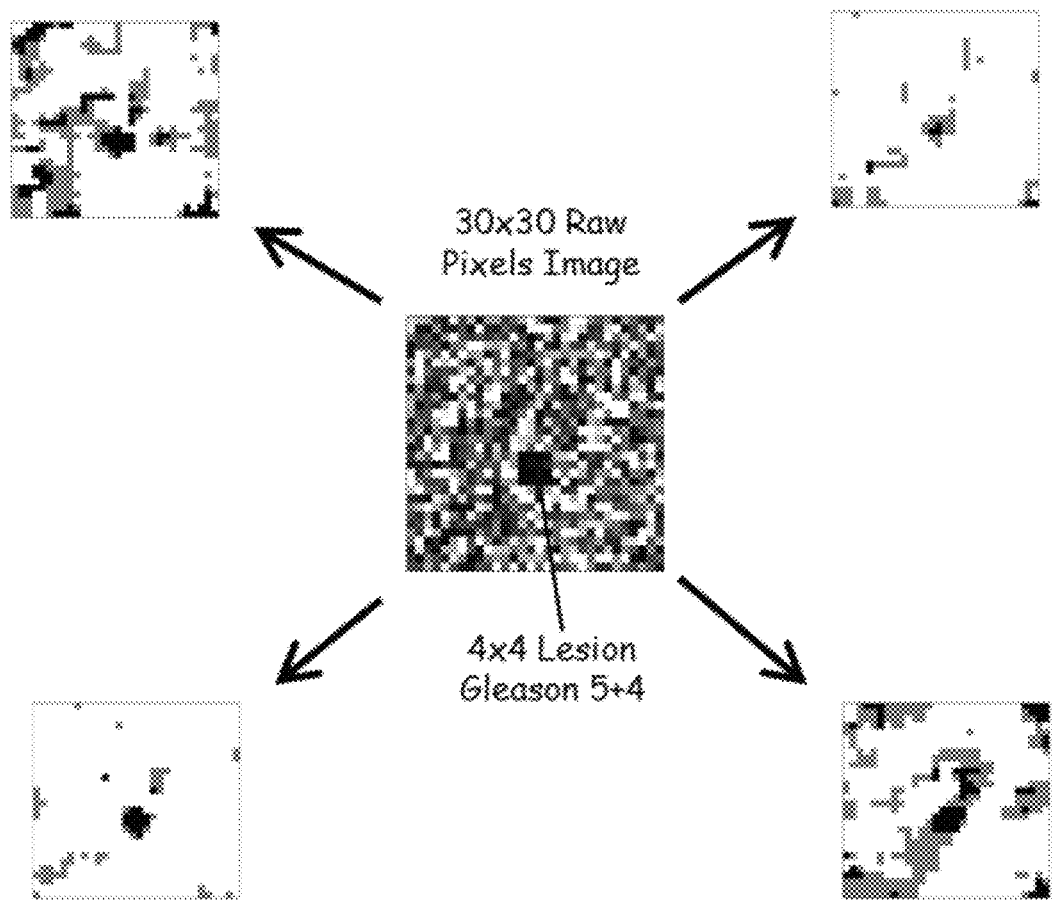
FIG. 23 shows examples of counting-statistics effects on processed images.

Representative examples of chemical element maps suitable for the present embodiments are provided in the Examples section that follows (see FIGS. 17, 22 and 23).

Method 330 continues to 336 at which calculating a gradient of chemical element over the map. Gradient calculation can be performed straightforwardly by subtracting the chemical element levels of two biopsy locations of the map and dividing by the distance between these biopsy locations. The method optionally and preferably proceeds to 337 at which the gradient is used for determining one or more additional biopsy location for a future biopsy. For example, when the element is zinc, the method can calculate a vector whose direction is the lowest zinc concentration and whose length is predetermined (e.g., half the distance between two adjacent biopsy locations). The additional biopsy location can be determined using the biopsy location of lowest zinc level as a reference. Formally, denoting the biopsy location of lowest zinc level as $x_0$ and the vector by $\underline{r}$ the additional biopsy location can be set to $\underline{x_0}+\underline{r}$, where underlined letters represent vectorial quantities.

At this additional biopsy location, the physician can then extract an additional biopsy core.

In some embodiments of the present invention the method continues to 338 at which a location and optionally also size of a tumor in the prostate is estimated. This can be done based on the chemical element levels in various regions in the prostate as known in the art. For example, when the prostate has a region in which the zinc levels are low, the method can determine that there is likelihood that the region includes a tumor.

In some embodiments of the present invention the method continues to 339 at which a grade of a prostate cancer is estimated from the chemical element map. The grading can be for example, using the Gleason scoring system. The grading can be accomplished by any technique or set of criteria known in the art. Preferably, but not necessarily, the grading is done automatically. For example, the grading can be done according to the teachings of International Patent Publication No. WO2009/083988 the contents of which are hereby incorporated by reference. A representative technique for grading the cancer is provided hereinunder.

In various exemplary embodiments of the invention the method continues to 340 at which the biopsy locations, chemical element map and/or additional biopsy location is displayed on an image of the prostate, e.g., by means of a display device. The method can also display the grading results.

In various exemplary embodiments of the invention the method continues by iteration whereby, at each iteration phase, the level of the chemical element from the most recent biopsy core is measured and the dataset is updated by adding thereto the biopsy location and chemical element level of the most recent core. This iteration is schematically represented by a loop-back arrow in FIG. 33. It is to be understood that although the loop-back arrow in FIG. 33 is shown from 340 to 332, this need not necessarily be the case. The method can loop back from any other block, e.g., 337, 338 and 339.

The method ends at 341.

Reference is now made to FIGS. 34A-D which are schematic illustrations of a system 400 for analyzing a plurality of biopsy cores extracted from a plurality of respective biopsy locations in a prostate, according to various exemplary embodiments of the present invention. System 400 comprises a stage 411, for holding the biopsy cores 401 in addressable XY locations on stage 411, wherein the addressable XY locations respectively correspond to the biopsy locations in the prostate.

Each of cores 401 can be positioned on stage 411 within a core holder 405. Core holders can be arranged on a moisturizing tray 402 which can be placed on stage 411.

System 400 further comprises an irradiation-detection system 440, configured for irradiating the addressable locations by a beam 442 of exciting radiation and detecting fluorescent x-ray radiation emitted from chemical element in the respective biopsy cores 401. Typically, system 440 comprises an X-ray tube 413 which generates beam 442 and a detector 414 which detects the emitted radiation as known in the art.

Although system 440 is shown to produce a single beam 442 this is not necessarily be the case, since for some application it may be desired to employ more than one beam of exciting radiation.

The energy of beam 442 emitted from tube 413 is dictated by the energy behavior of the cross-section for the excitation of a given element and by the absorption in the gland tissue. For example, if the chemical element is zinc, the optimized incident energy is between 18 and 23 KeV. When a filtered X-ray tube is used the energy depends on the anode material and the filtration of the continuous Bremsstrahlung radiation. In this case several anodes may be used, for example a molybdenum anode with a characteristic emission line of 17.4 keV, a Zr with a characteristic emission line of 15.8 keV or a Nb anode with a characteristic emission line of 16.6 keV. All this is well known to those skilled in the art of nuclear medicine.

Detector 414 can be of any type. For example, the detector may be a high energy-resolution solid state detector such as, but not limited to, detectors based on Silicon (Si), Germanium (Ge), Silicon-Lithium-drifted (Si(Li)), Ge(Li), Mercury Iodide ($HgI_2$) or Cadmium-zinc Telluride (CdZnTe), which can be cooled by a small thermoelectric device. Detector 414 may optionally be a high energy-resolution gaseous detector such as, but not limited to, a gas proportional detector or gas scintillation detector. It is to be understood that any other detector sensitive to X-rays in general and to a characteristic X-ray fluorescence emitted by the chemical element is not excluded from the scope of the present invention. The detector can optionally be a single element, a pixelized array or an array assembled of many individual elements. A solid state detector can optionally be a PIN diode, a surface barrier diode, a drift diode, a micro-strip detector, a drift chamber, a multi-pixel detector, a multi-strip detector and others.

Optionally and preferably detector 414 also detects Compton scattered x-rays from the biopsy cores. The Compton scattered x-rays can be used for normalization. For a given configuration and fixed beam intensity, the intensity of the scattered x-rays depends on the average constitution of the biopsy cores and can therefore serve as a normalization factor between different measurements for tissues from different cores and different patients. In some embodiments of the present invention apparatus the normalization includes detecting of an additional chemical element referred to herein as a reference element. In these embodiments, the level of the element of interest is determined relatively to reference element.

System 440 preferably transmits chemical element data to a processing system 450 responsively to the detected radiation.

Stage 411 and system 440 are preferably placed in a measuring chamber 412 encapsulated by an x-ray shield for the operator protection. At least one of stage 411 and system 440 is movable. Optionally and preferably, system 400 comprises a biopsy device interface 420 which facilitates automatic removal of the core from the biopsy device. The removal of core can be done by controlling stage 411 such that the respective location on tray 411 is under interface 420.

System 400 further comprises a controller 416 which controls the relative motion (linear, circular or any combination therebetween) between stage 411 and irradiation-detection system 440 such that beam 442 scans stage 411. The initial XYZ position of stage 411 relative to system 440 is preferably selected such that detector 414 receives radiation from the groove 406 of one of the core holders 405.

Controller 416 preferably transmits core identification data to processing system 450 synchronously with the scan. The core identification data can comprise the XY location of the core on stage 411 or any other type of identification data, such as, but not limited to, coded data such as serial numbers of the cores and the like.

In various exemplary embodiments of the invention processing system 450 receives the biopsy locations as input, e.g., and via an operator console 418. Processing system 450 preferably generates a chemical element map of at least a portion of the prostate based on combined information which includes the chemical element data (received from 440), core identification data (received from controller 416) and the biopsy locations (received as input). The relative motion between stage 411 and system 440, the detection of chemical element and the generation of map is preferably generated automatically. Processing system 450 can also use the chemical element data for provided by system 440 for determining the size of the respective core.

In some embodiments of the present invention processing system 450 also calculates a gradient of chemical element over the map. Based on the gradient, system 450 can determine one or more additional biopsy locations for a future biopsy, as further detailed hereinabove. Processing system 450 can also control a display device (not shown, see for example, FIG. 31) to display the biopsy locations, chemical element map, and/or additional biopsy location(s) on an image of the prostate. In some embodiments of the present invention, processing system 450 estimates the location and optionally size of a tumor in the prostate, as further detailed hereinabove.

System 400 can optionally comprise an imager 444 such as a CCD or a bar-code reader. Imager 444 can serve for identifying the location of the core on tray 411, hence reduces human error in placing the cores on tray 411. Imager 444 can also be used for obtaining visual information such as color or size of the biopsy cores. Imager 444 preferably transmits image data to an image processor 417 which may communicate with system 450.

Figure 35:
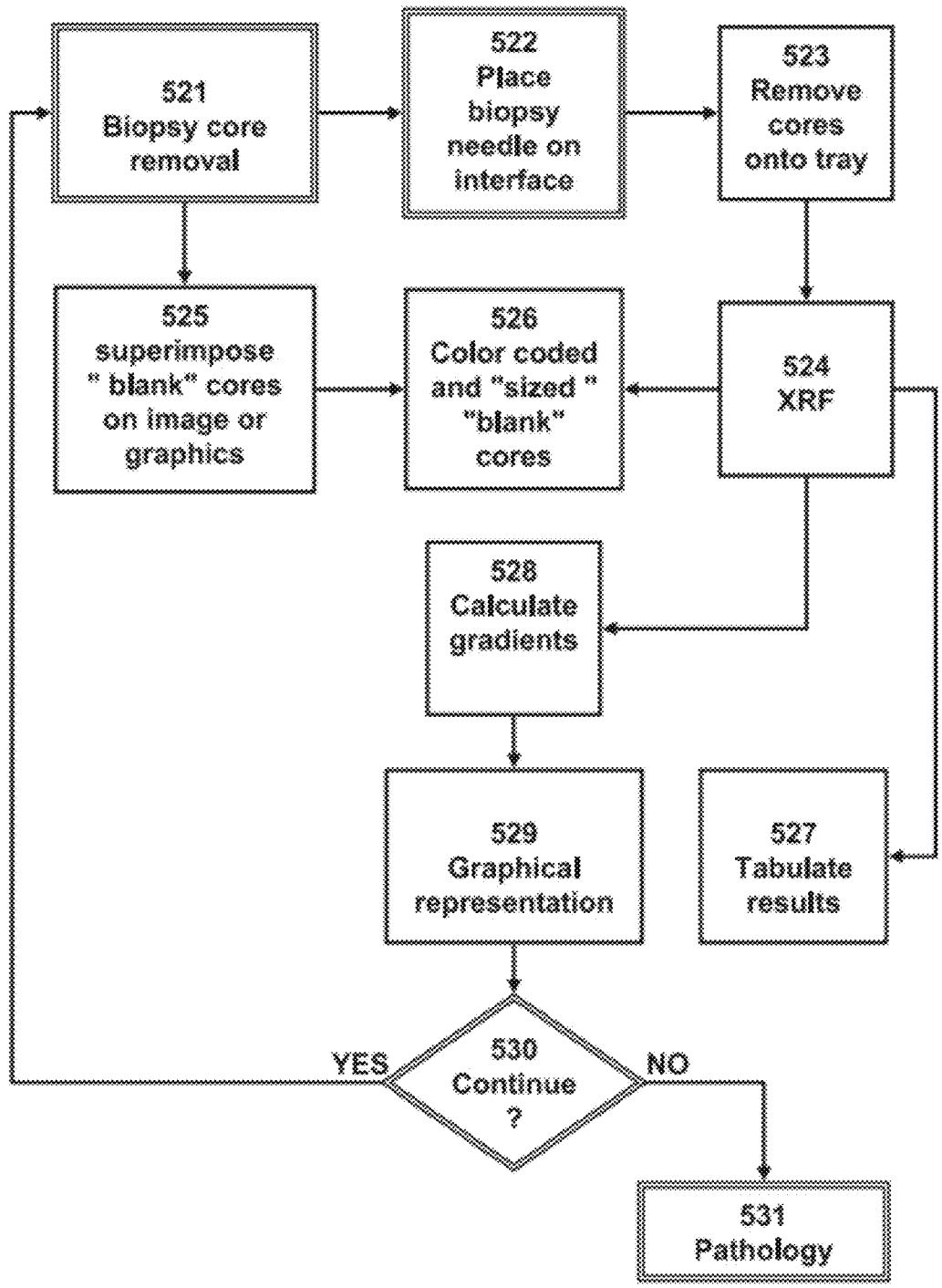
FIG. 35 is a flowchart diagram of a biopsy procedure, according to some embodiments of the present invention.

FIG. 35 is a flowchart diagram of a procedure which incorporates system 400 and method 330, according to various exemplary embodiments of the present invention. The procedure describes real time guidance, detection and grading of biopsy cores during a prostate biopsy session. In the flowchart diagram, double-line blocks represent manual operation and single-line blocks represent automatic operation.

At 521 a biopsy core is removed from the prostate, e.g., by TRUS, while the urologist is looking at the screen of the Ultra Sound system to different prostate locations and depths. At 522 the biopsy needle containing the core is then immediately placed onto the interface 420 in measurement chamber 412. At 523 the core is automatically removed from the needle onto the tray 402, and at 524 the XRF measurement is performed. As the XRF identifies the start of the core through the measurement of x-ray fluorescence, the XRF also provides information about what is the length of the core. This operation is referred to herein as sizing.

At 525 the zinc distribution in the core as measured by the XRF system is translated into a color coded graphical representation of the core on the screen. The positions of the needles are also defined towards fiducials in the organ either on the ultrasound image imported from the TRUS or a graphical representation of the Prostate. These positions are referred to as "blanks", as apart from the location the apparatus does not necessarily include any further information about the cores before they undergo the XRF measurement. At 526 the blanks are compiled together with the XRF information. Preferably the complied information is presented in a color coded representation, e.g., using a display device. At 527 the zinc distribution measured in the core is incorporated into a table containing the data for all the cores.

The more aggressive the cancer site (e.g., higher Gleason Grade), the lower the zinc level for that site. Additionally, Non-PCa tissue close to a PCa site is characterized by a lower zinc level than the average level for benign tissue, although the zinc depletion for such a case is not as pronounced as for PCa tissue. Additionally, the higher the grade of a PCa tumor, the more pronounced is zinc depletion in Non-PCa tissue close to that tumor.

At 528 the zinc gradients are calculated. After performing 2-4 biopsies, the procedure is able to present a gradient vector as further detailed hereinabove. Typically, the length of such vector is, without limitation, about 1 mm. Based on this vector, the procedure recommends the physician to change the initial random biopsy plan and instead to poke next where the odds to hit a tumor are the highest. The procedure continues recommending the next biopsies locations until the whole prostate is covered. The recommendations can include also denser poking in places where the vectors calculation indicates a large tumor. The recommendations can also include locations near a tumor already identified in order to increase the number of positive cores. The type of recommendation (in a tumor or near a tumor) can be also dictated by the physician, for example, using console 418.

At 529 the recommendation for biopsy locations is presented using a graphical representation of the prostate or an image thereof, so as to help the physician hit the alternative site as accurately as possible.

After completion of operations 521-529 or part thereof, the physician decides, at 530, whether or not to extract a biopsy core at a different site. Accordingly, the physician can decide to remove additional biopsy cores from a region around a site where high Gleason grade was found, for better characterization of size and extent of the tumor at that site. The physician can decide to remove additional biopsy cores from sites distanced from a site where a tumor was found, in order to verify whether the PCa is localized or not. The physician can decide to continue with the biopsy even though no tumors were found in any biopsy core, according to the average zinc levels or local zinc levels measured, which may correspond to low grade tumor (for instance Gleason <6), or may be indicative or pre-malignant metabolism.

In case further cores are to be extracted the procedure loops back to 521. In case no further cores are to be extracted, the procedure optionally proceeds to 431 at which all the cores removed until that point and collected into tray 402 can be sent together for pathology. The physician may also send the biopsy report, incorporating the tabulated results (obtained at 527) and the graphic representation image (obtained at 529) with the color coded XRF findings (obtained at 526) in the package for the pathologist.

Figure 25:
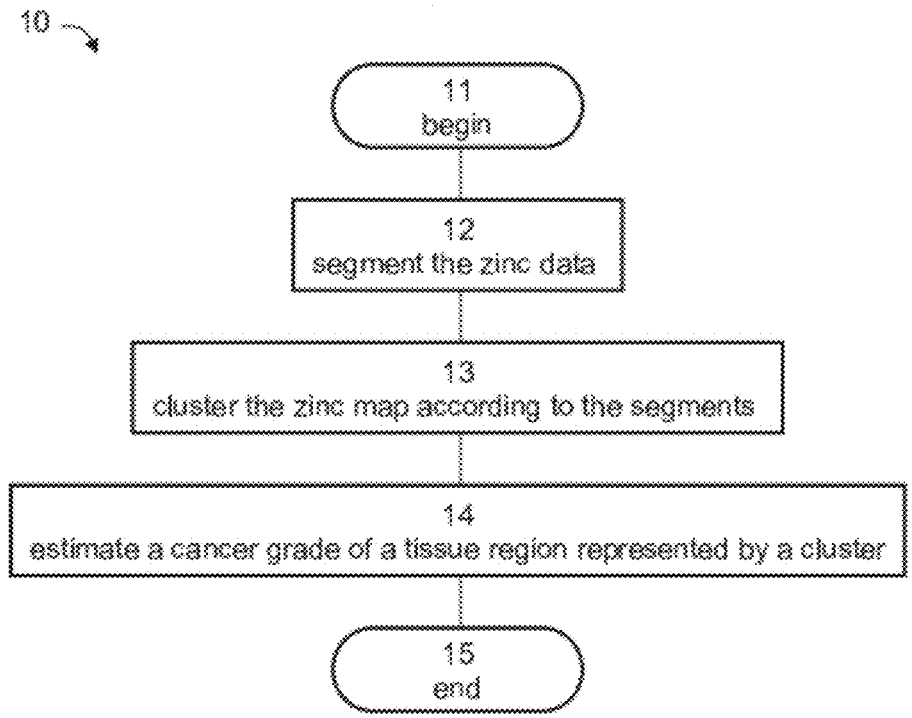
FIG. 25 is a flowchart diagram of a method suitable for estimating a prostate cancer grade, according to various exemplary embodiments of the present invention.

FIG. 25 is a flowchart diagram of a method 10 suitable for estimating a prostate cancer grade, according to various exemplary embodiments of the present invention. The method can be used for executing operation 339 of method 330.

Method 10 begins at 11 and optionally and preferably continues to 12 at which the chemical element data, e.g., zinc data, are segmented into a plurality of segments, each corresponding to a predetermined range of zinc levels.

The result of the segmentation operation 12 is a plurality of segments, each defined as a range of zinc values (concentrations, amounts, grey levels, or some normalized values thereof). The segments are preferably mutually exclusives, namely that there is no overlap between segments. Each zinc value over the zinc data preferably belongs to one segment.

Since the zinc data is represented by a zinc map, each picture-element of the map is also associated with one of the segments. Specifically, all picture-elements having zinc values which are within a range of zinc values defining a particular segment are said to be associated with that segment. Formally, denoting the ith segment by $s_i$ and the range of zinc values which defines $s_i$ by $R_i$, the set $P_i$ of picture-elements which are associated with $s_i$ includes all picture-elements which have a zinc value g satisfying g∈$R_i$.

It is noted that although the zinc map includes zinc information as well as spatial information, the segmentation is according to the zinc values and not the spatial location of the picture-elements in the map. Therefore, picture-elements which are associated with a segment do not necessarily reside on the same region of the prostate. On the other hand, the zinc data of all picture-elements associated with a segment are within the same range of zinc values.

The number of segments can be predetermined or it can be determined by method 10. The segmentation can be done according to the range of values within the zinc data or within a portion of the zinc data which is under investigation. The segmentation can be uniform across the range of zinc values. Suppose for example that there are N segments, and that the zinc data are digitized such that there are M different zinc values. In this embodiment, each segment can be defined over a range of approximately M/N zinc values. Without loss of generality, the zinc values can be integers from 1 to N. Denoting the N segments by $s_1, s_2, \ldots, s_N$, the first segment $s_1$ can include zinc data values from 1 to approximately M/N, the second segment $s_2$ can include zinc data values from approximately M/N+1 to approximately 2M/N, etc. The special case in which N=M (i.e., each segment is defined by a single zinc value) is not excluded from the scope of the present invention. Thus, the term "range of zinc values" as used herein also encompasses the case in which the range includes a single zinc value.

The segmentation can also be non-uniform, in which case the range of values for some segments is wider than the others. This embodiment is useful when the uniform segmentation results in some segments which are associated with a small number of picture-elements.

At 13 the method clusters the zinc map according to the zinc levels associated with the picture-element. The clustering operation takes into account the spatial information in the zinc map. The operation aims at partitioning the zinc map into multiple regions each of which being substantially homogeneous with respect to the zinc values of the picture-elements within the region. Preferably, the clustering is according to the predetermined segments. As stated, the zinc data of all picture-elements associated with a segment are within the same range. At 13 the method determines, for at least one of the segments, which of the picture-elements associated with the segment are sufficiently close to each other and identifies those picture-element as belonging to the same cluster. It is appreciated that there can be more than one cluster for a single segment since there can be more than one region in the prostate with the same average level of zinc. A representative example of the result of segmentation 12 and clustering 13 is provided in the Examples section that follows (see FIGS. 18A-C).

The clustering and the optional segmentation operations can be executed by any technique known in the art of data analysis and/or image processing. In some embodiments of the present invention the range of levels according to which the zinc data are segmented are determined dynamically during the clustering operation.

A representative example of a technique suitable for segmentation 12 and clustering 13 of the present embodiments is the expectation-maximization (EM) technique [Ramos et al., LNCS 1923 319-323, 2000]. In this embodiment the zinc data are digitized and partitioned into N homogeneous clusters classified by their average zinc values. EM is an unsupervised algorithm, which iteratively alternates between segmenting the map into N clusters and characterizing the properties of each cluster in terms of its zinc value. The output image of the EM clustering algorithm is a statistical description of the N clusters, providing the number of components in each cluster, the localization of the cluster components within the map, the average zinc value and related variances associated to each cluster. Other clustering technique, such as, but not limited to, thresholding, Markov random fields, graph theory methods, density estimation methods, scale-space clustering and the like. Several such techniques are disclosed in Pham et al., "Current methods in medical image segmentation," Annu. Rev. Biomed. Eng. 2, 315-37, 2000.

The clustering operation is not necessarily executed for all the picture-elements of the zinc map. For example, it is not necessary to identify clusters of picture-elements which are associated with sufficiently high zinc levels (say, above 150 parts per million, since it is more likely that these picture-elements represent non-cancerous tissue regions in the prostate gland. In any event, clustering 13 results in at least one cluster of picture-elements.

At 14 a cancer grade of a tissue region represented by at least one cluster is estimated. In various exemplary embodiments of the invention the cancer grade is scaled according to the Gleason grading scale [Gleason, D F, Hum. Pathol. 23 273-279, 1992; Epstein et al., Am. J. Surg. Pathol. 29 1228-1242, 2005]. The Gleason grading scale assigns a combination of two grades (referred to herein as Gleason primary grads and Gleason secondary grade), each ranging from 1 (corresponding to highly-differentiated cells or low-aggressive cancerous pattern) to 5 (corresponding to poorly-differentiated cells or highly-aggressive cancerous pattern). Although the Gleason grading scale was developed for quantified analysis of pathological specimens, it is not intended to limit the scope of the present invention for pathology. As explained hereinunder and demonstrated in the Examples section that follows, the present Inventors discovered that the Gleason grading scale is suitable for grading the aggressiveness of the cancer based on zinc data collected in vivo. A detailed description of the Gleason grading scale is provided in the Examples section that follows.

The cancer grade is preferably estimated for clusters which correspond to a lowest range of zinc levels in the zinc data. In terms of the segmented data, $s_1, s_2, \ldots, s_N$ the cancer grade is preferably estimated for clusters which correspond to the first segment $s_1$ (i.e., the segments which is defined by the lowest range of zinc levels). The cancer grade is preferably estimated for other clusters as well. For example, in some embodiments of the present invention the cancer grade is estimated also for clusters which correspond to the next-to-lowest range of zinc levels (i.e., clusters corresponding to the second segment $s_2$). Estimation of cancer grades for other clusters (e.g., clusters corresponding to the next-to-next-to-lowest range of zinc levels or third segment $s_3$) is also contemplated. A cluster for which the cancer grade is estimated is referred to hereinunder as a "query cluster," and a cluster for which the cancer grade is not estimated are referred to hereinunder as a "background cluster." During execution of method 10, there can be one or more query clusters and any number (including zero) of background clusters.

The cancer grade is estimated based, at least in part, on zinc levels associated with the query cluster. Typically, but not necessarily, for the purpose of the grading, a representative zinc level is defined to for the query cluster. Such representative zinc level can be, for example, an average zinc level, including, without limitation, arithmetic average, geometric average, harmonic average, root-mean-square, generalized (arbitrary power) root-mean-power and the like. The average zinc level can be calculated as a weighted or non-weighted average. When a weighted average is calculated the weights can be related, for example, to Euclidian distances of the picture-elements of the query cluster from the center of the cluster. Also contemplated are other types of representative zinc levels, including, without limitation, a median zinc level, a zinc level of a central picture-element in the query cluster, etc.

The cancer grade of a tissue region which corresponds to the query cluster can be estimated in more than one level of estimation.

One level of estimation is a binary estimation, in which case the method roughly determines whether or not there is a malignant tumor in the prostate, and if so whether or not the cancer of the respective tissue region is aggressive. In this embodiment, it is sufficient to compare the average zinc level associated with the query cluster to a predetermined zinc level threshold. In this embodiment the method can compare the average zinc level (Zn) to a predetermined zinc level threshold, $L_1$, and determine that there is a high likelihood (above 50%) that the cancer is aggressive if the average zinc level is below $L_1$. For example, it was found by the present inventors that an average zinc level below 75 parts per million (ppm) indicates that it there is a high likelihood (above 50%) that that the cancer grade of the respective tissue region is equivalent to a Gleason grade having a primary grade which is at least 4. Thus, the value of the threshold $L_1$ can be 75 ppm, since a Gleason primary grade of 4 or more describes an aggressive cancer.

When it is desired to determine the likelihood for the presence of more aggressive cancer, the value of the threshold $L_1$ is preferably lower than 75 ppm. For example, it was also found by the present inventor that an average zinc level below about 45 ppm indicates that there is a high likelihood (above 90%) that the cancer grade is equivalent to Gleason score 9. Thus, the value of the threshold $L_1$ can be 45 ppm, since a Gleason score of 9 describes an aggressive cancer. It was further found by the present inventor that an average zinc level below about 30 ppm indicates that there is a high likelihood (above 90%) that the cancer grade is equivalent to Gleason grade 5+4. Thus, the value of the threshold $L_1$ can be 30 ppm, since a Gleason grade of 5+4 describes an aggressive cancer.

The term "Gleason score", as used herein, refers to the sum of the primary and secondary Gleason grades. Thus, for example, the Gleason score of Gleason grade 4+5 is 9.

The method can determine that the query cluster does not correspond to a malignant tumor if the average zinc level is above a predetermined threshold which is preferably higher than $L_1$. Alternatively, if the (Zn) is above $L_1$, the method can employ a different procedure such as, but not limited to, one or more of the procedures described hereinunder.

Once a binary estimation has been made, the method can issue a report regarding the estimation. The report can be provided in any visible way, for example, on a display device or a printed hard copy. The report can also be transmitted to a remote location to be displayed or printed at the remote location.

Figure 26:
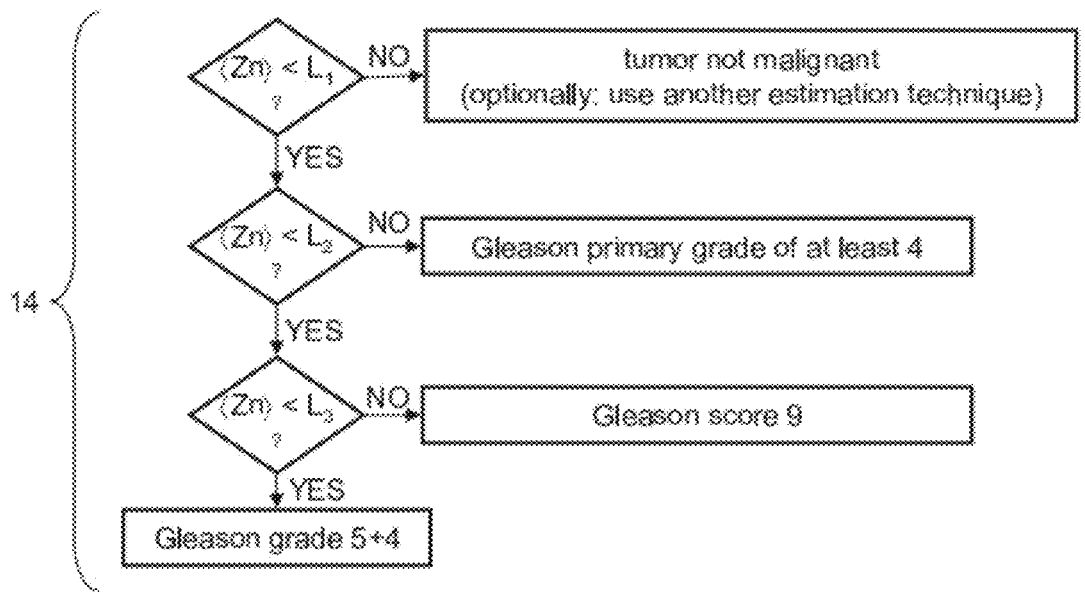
FIG. 26 is a flowchart diagram describing an embodiment of the invention according to which three zinc level thresholds are employed for differentiating between different aggressiveness levels of the cancer.

Combination of several predetermined zinc level thresholds, $L_1, L_2, \ldots, L_k$ ($L_1 > L_2 > \ldots > L_k$) is also contemplated. This embodiment provides non-binary estimation since it allows the differentiation between different aggressiveness levels of the cancer. A representative example of this embodiment, for the case of three zinc level thresholds, $L_1$, $L_2$ and $L_3$ is illustrated in FIG. 26. As shown, the method first compares the average zinc level (Zn) to first threshold $L_1$. If (Zn) is below threshold $L_1$, the method compares (Zn) to second threshold $L_2$. If (Zn) is also below threshold $L_2$, the method further compares (Zn) to third threshold $L_3$. Thus, the method determines whether (Zn) is between $L_2$ and $L_1$, between $L_3$ and $L_2$ or below $L_3$, and estimates the grade as follows: If (Zn) is between $L_2$ and $L_1$ the method determines that there is a high likelihood (above 50%) that the cancer grade is equivalent to a Gleason grade having a primary grade which is at least 4, if (Zn) is between $L_3$ and $L_2$ the method determines that there is a high likelihood (above 50%) that the cancer grade is equivalent to a Gleason score 9, and if (Zn) is below $L_3$, the method determines that there is a high likelihood (above 90%) that the cancer grade is equivalent to a Gleason grade 5+4. Representative examples of the thresholds $L_1$, $L_2$ and $L_3$ are about 75 ppm, about 45 ppm and about 30 ppm, respectively. Once such non-binary estimation has been made, the method can issue a report regarding the estimation; as further detailed hereinabove.

The method can determine that the query cluster does not correspond to a malignant tumor if the average zinc level is above a predetermined threshold which is preferably higher than any of the thresholds used for differentiation between different aggressiveness levels of the cancer. Alternatively, if the (Zn) is above the highest threshold (e.g., $L_1$ in the above example), the method can employ a different procedure such as, but not limited to, one or more of the procedures described hereinunder.

Another level of estimation according to some embodiments of the present invention allows a more fine differentiation between the various grades. This can be done in more than one way, as will now be explained.

In some embodiments, the estimation of cancer grade is based on a predetermined dependence of the cancer grade on: (i) a size of said cluster and (ii) zinc levels or a representative zinc level associated with the cluster. For example, the predetermined dependence can be expressed as a plurality of predictive geometrical loci in a two-dimensional plane, where each locus corresponds to a different cancer grade (e.g., a different Gleason grade or score). Thus, in this embodiment, the cancer grade can be selected from a predetermined set of cancer grades.

Figure 21:
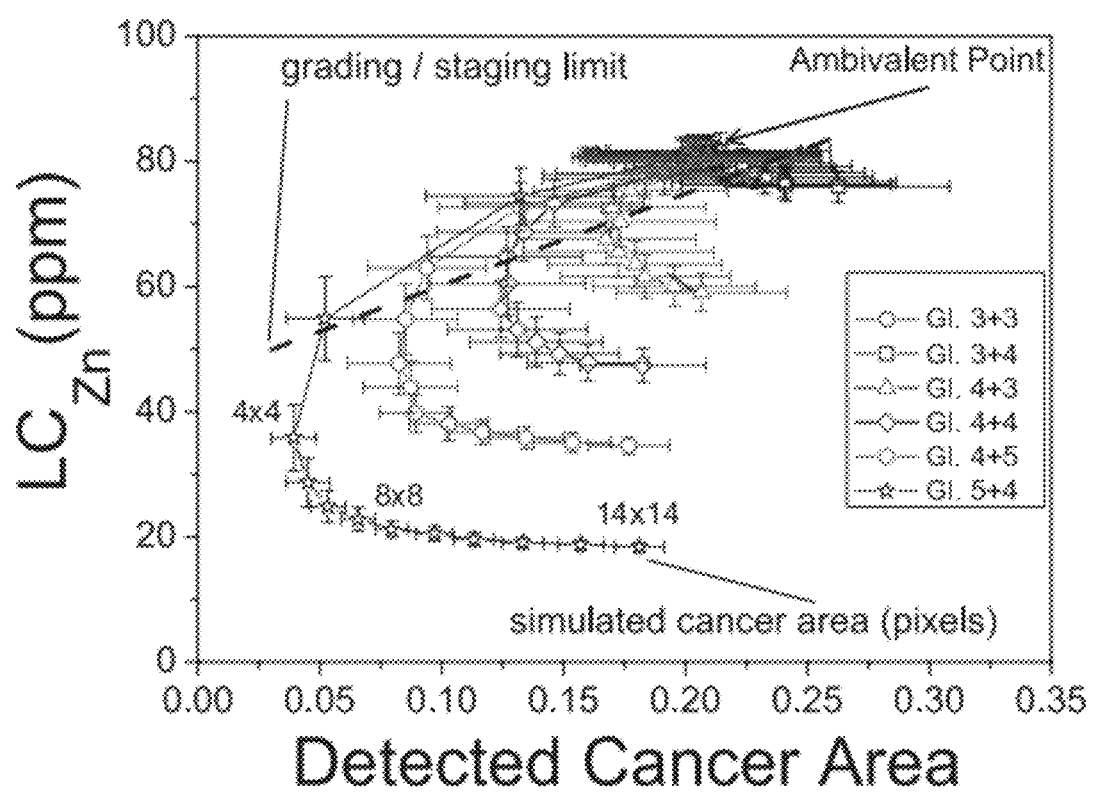
FIG. 21 shows the relationship between average zinc level in the detected lesion and the detected cancer area (expressed in units of fraction of the total map area), for various Gleason grades, according to various exemplary embodiments of the present invention.
Figure 27:
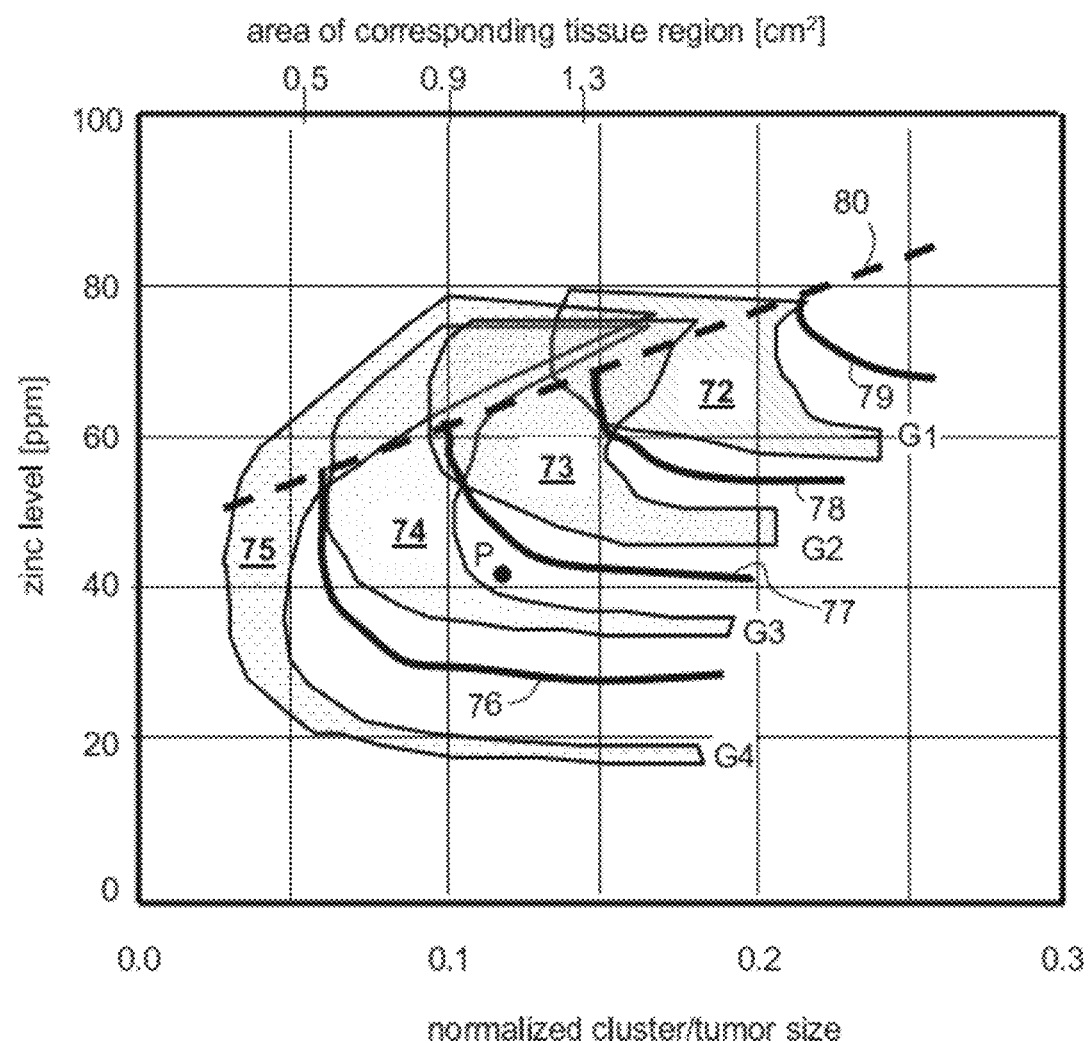
FIG. 27 is a schematic illustration of predictive loci, which can be used for estimating a prostate cancer grade, according to various exemplary embodiments of the present invention.

A representative example of such predictive loci is illustrated in FIG. 27 and further demonstrated in the Example section that follows (see FIG. 21).

Referring to FIG. 27, four predictive loci 72-75 are shown in a two-dimensional plane spanned by a zinc level axis and a cluster/tumor size axis. As shown, each locus has a planar shape in the plane. The cluster or tumor size is conveniently displayed in normalized dimensionless units representing fractions of the total area of the zinc map or, equivalently, total cross-sectional area of the prostate from the view point from which the zinc data was acquired. Also displayed in FIG. 27 is the area of the corresponding tissue region. One of ordinary skill in the art provided with this description would know how to construct the loci using other types of presentations for the size of the cluster or corresponding tissue region.

Loci 72-75 respectively correspond to a set of four predetermined cancer grades, denoted in FIG. 27 by G1, G2, G3 and G4. For example, G1 can be equivalent to Gleason grade 4+3, G2 can be equivalent to Gleason grade 4+4, G3 can be equivalent to Gleason grade 4+5 and G4 can be equivalent to Gleason grade 5+4. More loci and corresponding grades are also contemplated.

To estimate the cancer grade of a tissue region, the method can determine the representative zinc level and size of the respective query cluster. The zinc level and size is a point P in the two-dimensional plane of the loci. The method then searches for the closet locus to the fit this point and estimate the grade based on the results of the search. The method can also weight the likelihood of the estimation using the distance between the point and the found locus. For example, if the point is on the locus, the method can determine that the likelihood for the corresponding tumor to have the respective grade is, say at least 70%, and if the point is near the locus, but not on it, the method can determine that the likelihood for the corresponding tumor to have the respective grade is between 50% and 70%.

In the exemplified illustration of FIG. 27 P is close to locus 74 which correspond to grade G3. In this case, the method can determine that there is a high likelihood (e.g., from about 50% to about 70%) that the grade of the corresponding tissue region is G3.

In various exemplary embodiments of the invention the loci can be separated by boundary lines 76-79 for delineating the boundary between two adjacent loci. In the representative example illustrated in FIG. 27, boundary lines 76-79 represent equal-likelihoods for the respective grades. For example, when point P lies on or being close to, say boundary line 77 which separate between locus 73 (corresponding to grade G2) and locus 74 (corresponding to grade G3), the method can estimate that the likelihood that the grade is G2 equals the likelihood that the grade is G3. Boundary lines 76-79 can also be used according to some embodiments of the present invention for thresholding. For example, when point P is below line 76 the method can determine that there is a likelihood of at least 50% that the grade of the corresponding tissue region is G4, when point P is between line 76 and line 77 the method can determine that there is a likelihood of at least 50% that the grade of the corresponding tissue region is G3, when point P is between line 77 and line 78 the method can determine that there is a likelihood of at least 50% that the grade of the corresponding tissue region is G2, and when point P is between line 78 and line 79 the method can determine that there is a likelihood of at least 50% that the grade of the corresponding tissue region is G1.

In regions which are above line 79 the method preferably estimates that there is a likelihood of at least 50% that the corresponding tissue region is benign or has a low cancer grade (e.g., Gleason primary grade of 3 or less). Same estimation can also be used when the average zinc level is above 80 ppm.

In various exemplary embodiments of the invention the loci include a prediction threshold line 80. Above line 80, there are regions at which some of the loci 72-75 overlap. When point P lies above line 80 and in a region that, say, locus 74 (corresponding to grade G3) and locus 75 (corresponding to grade G4) overlap, the method can determine there is a high likelihood (above 50%) that the grade of the corresponding tissue region is G3 or G4. In other words, instead of assigning one of the predetermined grades, the method assigns the sub-set {G3, G4} ⊂ {G1, G2, G3, G4} to the corresponding tissue region.

Generally, line 80 can be used for two-dimensional thresholding. In this embodiment, when point P is below line 80 the method determines (with likelihood of at least 50%) that the grade of the corresponding tissue region is one grade of the predetermined set of grades, but when point P is above line 80 the method assigns a set of two or more grades to the corresponding tissue region. The method can also provide weights for each of the grades in the assigned set. Typically, for smaller clusters the higher grades (e.g., G3 or G4) dominate the assigned set and for larger clusters the less high grades (e.g., G1 or G2) dominate the assigned set.

Following the estimation of the cancer grade (in cases in which the method estimates that corresponding tumor is malignant), the method can issue a report regarding the estimation, as further detailed hereinabove. Optionally, the report also includes the estimated size of the corresponding tumor, thereby estimating the stage of the cancer.

In some embodiments of the present invention, a double classification technique is employed for estimating the cancer grade. In these embodiments, the query cluster is classified according to its zinc levels as well as its size (or, equivalently, the size of the corresponding tissue region), and the cancer grade is estimated based on both classifications. Double classification can be done using a plurality of predetermined zinc value thresholds and a plurality of size thresholds. For example, the representative zinc level of the query cluster can be classified according to the zinc level thresholds and a size of the query cluster or the corresponding tissue region can be classified according to a plurality of cluster size or tissue size thresholds.

Figure 28:
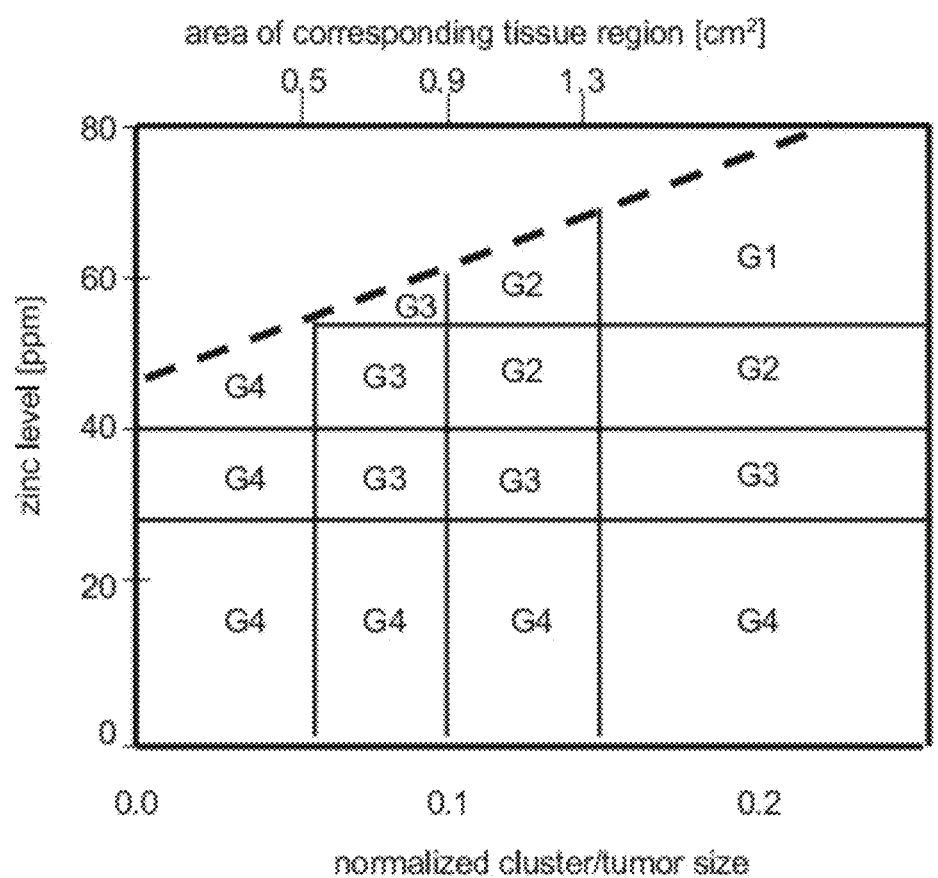
FIG. 28 is a schematic illustration showing two sets of thresholds which can be used for estimating a prostate cancer grade, according to various exemplary embodiments of the present invention.

A representative example of two sets of thresholds is illustrated in FIG. 28. The sets are ordered such as to form a grid in the two-dimensional plane spanned by the zinc level and cluster/tumor size axes. The cluster or tumor size is conveniently displayed in normalized dimensionless units representing fractions of the total area of the zinc map or, equivalently, total cross-sectional area of the prostate from the view point from which the zinc data was acquired. Also displayed in FIG. 28 is the area of the corresponding tissue region. One of ordinary skill in the art provided with this description would know how to define the two sets of thresholds using other types of presentations for the size of the cluster or corresponding tissue region.

The grid defines a plurality of regions, each defined between two successive zinc level thresholds of the set and two successive size thresholds of the set. Each region in the grid provides estimation for one cancer grade. In the representative example of FIG. 28, four cancer grades G1, G2, G3 and G4 are shown. For example, G1 can be equivalent to Gleason grade 4+3, G2 can be equivalent to Gleason grade 4+4, G3 can be equivalent to Gleason grade 4+5 and G4 can be equivalent to Gleason grade 5+4. Each region can represent a probability of, say about 70%, of having the respective grade. More predetermined grades are also contemplated. To estimate the cancer grade of a tissue region according to the present embodiments, the method can determine the point P which corresponds to the representative zinc level and size of the respective query cluster as further detailed hereinabove. The method then estimates the grade based on the relation between P and the thresholds (or equivalently the location of P in terms of the grid). The procedure can also include two-dimensional thresholding using prediction threshold line 80, as further detailed hereinabove.

Following are several examples for a double (zinc level and cluster or tissue size) classification, according to various exemplary embodiments of the present invention. The classifications are provided in terms of areas of the tissue region rather that the size of the cluster, but one of ordinary skill in the art would know how to express the classifications in terms of cluster size.

If P corresponds to a tissue region size which is above about 0.5 cm$^2$, and an average zinc level of from about 30 ppm to about 70 ppm the method can determine that there is a high likelihood (e.g., above 50%) that the grade is equivalent to a Gleason grade having a primary grade which is 4.

If P corresponds to a tissue region size which is from about 0.5 cm$^2$ to about 0.9 cm$^2$, and an average zinc level of from about 40 ppm to about 55 ppm the method can that there is a high likelihood (e.g., above 50%) that the grade is equivalent to a Gleason 4+5.

If P correspond to a tissue region size which is not below 0.9 cm$^2$, and an average zinc level of from about 40 ppm to about 55 ppm, more preferably from about 45 ppm to about 55 ppm the method can determine that there is a high likelihood (e.g., above 50%) that the grade is equivalent to a Gleason 4+4.

If P correspond to a tissue region size which is above 1.3 cm$^2$, and an average zinc level of from about 55 ppm to about 70 ppm the method can determine that there is a high likelihood (e.g., above 50%) that the grade is equivalent to a Gleason 4+3.

Once the grade is estimated based on the geometrical loci or double classification, the method can issue a report regarding the estimation; as further detailed hereinabove. Optionally, the report also includes the estimated size of the corresponding tumor, thereby estimating the stage of the cancer.

The method can also employ an iterative procedure for determining whether or not the query cluster correspond to a malignant tumor and estimating the cancer grade if the tumor is likely to be malignant. The iterative process generally includes two or more iterations where, for a given iteration, the cluster size is re-calculated based on a previously estimated grade. It is recognized that there is a correlation between the level of accuracy of the calculated cluster size and the degree by which the cluster is distinguishable from the background. It was found by the present inventors that this the level of accuracy is higher for high cancer grades than for low cancer grades. Thus, the method can use the cancer grade which was estimated in a previous iteration as the input for calculating of the cluster size, thereby to increase the accuracy level of the calculation.

The method ends at 15.

Figure 29:
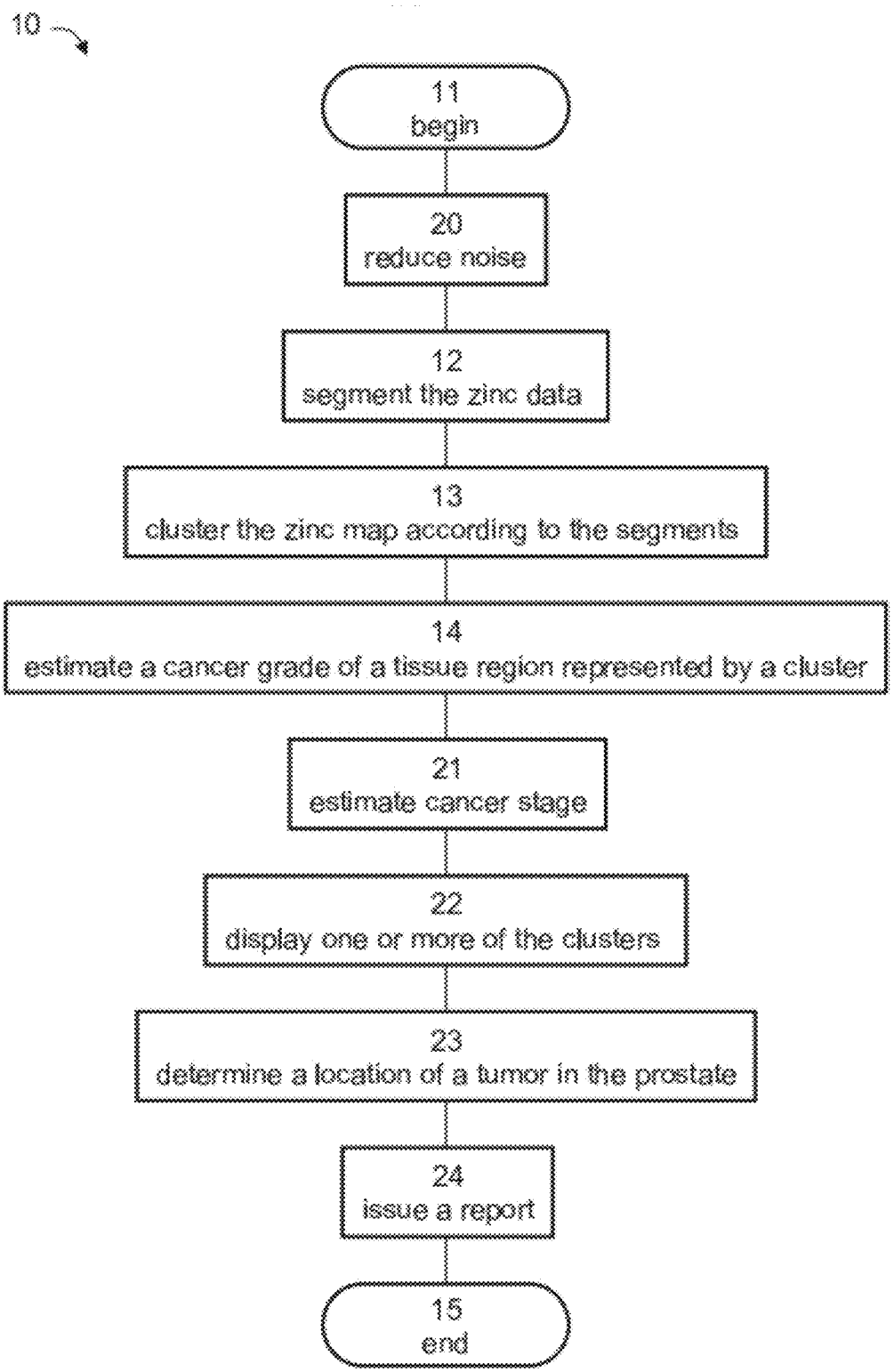
FIG. 29 is a flowchart diagram of a method suitable for estimating a prostate cancer grade in embodiments in which the method comprises one or more additional and optional operations.

FIG. 29 is a flowchart diagram of method 10 in embodiments in which the method comprises one or more additional and optional operations. In these embodiments, the method 10 begins at 11 and optionally and preferably continues to 20 at which a noise reduction procedure is employed. This can be done, for example, using a median filter. Preferably, the procedure is done so as to preserve the edges of the zinc map. The dimension of the median filter can be selected according to quality of the zinc data. A typical example of a median filter is a 5×5 median filter.

Optionally and preferably, the method continues to 12 at which the zinc data are segmented and/or 13 at which the method clusters the zinc map as further detailed hereinabove. The method can then proceed to 14 at which the cancer grade of a tissue region represented by the query cluster is estimated, as further detailed hereinabove.

In some embodiments of the present invention the method continues to 21 at which the method estimates the stage of the cancer. Staging can be done based on the estimated size of the tissue region which corresponds to the query cluster and on the location of these tissue regions.

In some embodiments of the present invention the method continues to 22 at which one or more of the clusters are displayed on a display device such as a computer screen, a printing device or the like. Both query clusters and background clusters can be displayed, if desired. Operation 22 can be executed before, after or during operation 14.

In some embodiments of the present invention the method continues to 23 at which the method determines a location of a tumor in the prostate. This embodiment is particularly useful for the physician, for example, when it is desired to access the tumor, e.g., for treatment or biopsy purposes. Tumor location can be calculated in any way known in the art. For example, when the boundaries of the zinc image correspond to the boundaries of the prostate gland, the location of the query cluster relative to the boundary of the zinc image can be used for determining the relative location of the tumor in the prostate.

In some embodiments of the present invention the method continues to 24 at which the method issue a report regarding the analysis. The report can include grade information and/or tumor location information and/or staging (e.g., tumor size) information. The report can be in graphical and/or alphanumeric form, as desired. For example, the report can be in the form of a map describing the prostate or a portion thereof, on which the locations of one or more tumors with their grades can be marked. The report can be provided in any visible way, for example, on a display device or as a printed hard copy. The report can also be transmitted to a remote location to be displayed or printed at the remote location.

The method ends at 15.

Figure 30:
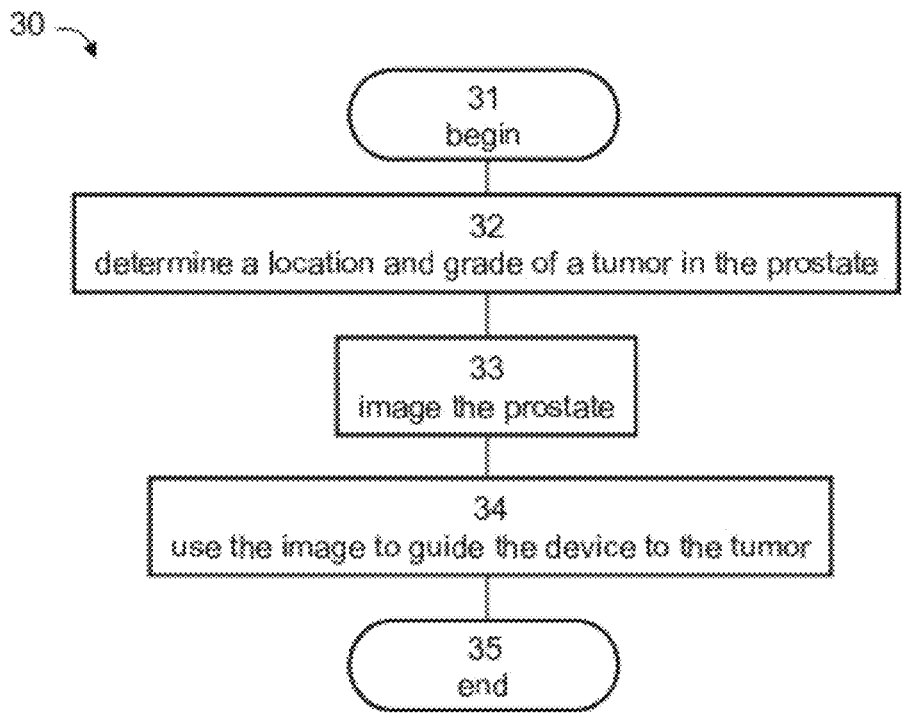
FIG. 30 is a flowchart diagram describing a method suitable for guiding an invasive medical device in a prostate, according to various exemplary embodiments of the present invention.

Reference is now made to FIG. 30 which is a flowchart diagram describing a method 30 suitable for guiding an invasive medical device in a prostate, according to various exemplary embodiments of the present invention. The medical device can be a biopsy needle device or a treatment device such as, but not limited to, a photodynamic therapy device. This method is preferably executed following execution of method 10 and is useful for targeted biopsy or treatment of a cancerous tumor.

Method 30 begins at 31 and continues to 32 at which a location and grade of a tumor in the prostate is determined as further detailed hereinabove, e.g., by executing selected operations of method 10. Method 30 optionally continues to 33 at which the prostate is imaged and the location is marked on the produced image. The imaging can be done by employ any imaging modality, include, without limitation, ultrasound imaging, CT, MRI and the like. The imaging can also be done or be supplemented with XRF for mapping the zinc levels in the prostate and optionally using these levels to generate the image. The location of the tumor on the image can be marked by matching the location of the query cluster in the zinc map to a location in the prostate image, as further detailed hereinabove. When the zinc map used by method 10 also includes an image of the prostate, the image acquired at 33 can be used as supplementary information. Alternatively, 33 can be omitted.

The method continues to 34 at which the method uses the prostate image for guiding the biopsy or treatment device to the tumor. The device is preferably introduced into the prostate while imaging such that the image presents the location of the device relative to the marked location of the tumor. This allows the physician to monitor the procedure and advance the device within the prostate in the direction of the tumor.

The method ends at 35.

Figure 31:
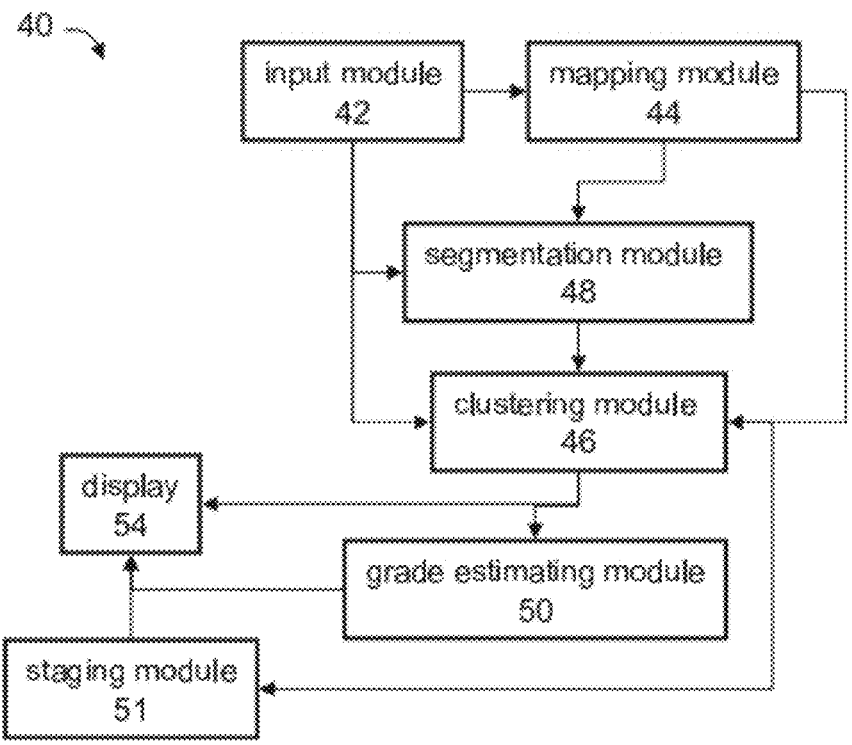
FIG. 31 is a schematic illustration of a system for estimating a grade of a prostate cancer, according to various exemplary embodiments of the present invention.
Figure 32:
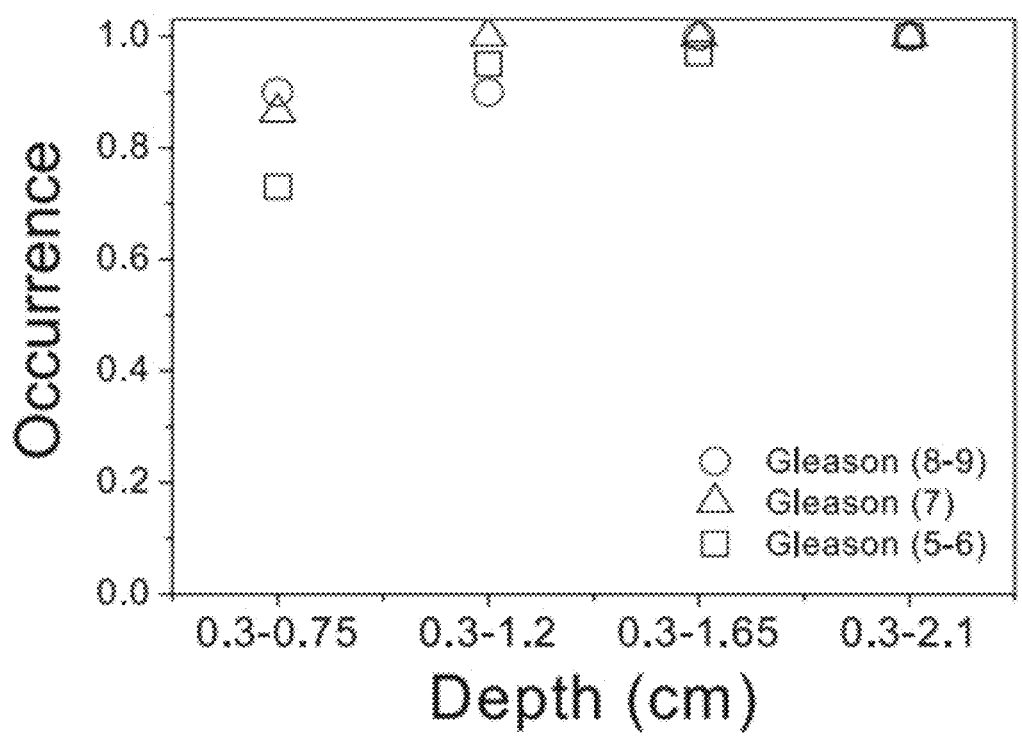
FIG. 32 shows occurrence that a PCa patient has at least one PCa segment within a given depth range, for various Gleason scores. The indicated depth in FIG. 32 includes 0.3 cm rectal wall thickness.

Reference is now made to FIG. 31 which is a schematic illustration of a system 40 for estimating a grade of a prostate cancer. Data flow within the various modules is shown by arrows. System 40 can be embodied, for example, in a computer readable medium. System 40 can be incorporated, for example in processing system 450 of system 400 described above.

System 40 comprises an input module 42, which receives the zinc data. In various exemplary embodiments of the invention system 40 further comprises a mapping module 44 which for generates a zinc map using the zinc data, as further detailed hereinabove. Alternatively, input module 42 can receive the zinc map.

System 40 further comprises a clustering module 46 which clusters the zinc map according to zinc levels, as further detailed hereinabove. Optionally, the system comprises a segmentation module 48 which segments the zinc data as further detailed hereinabove. System 40 further comprises a grade estimating module 50 which estimates the cancer grade as further detailed hereinabove. Optionally, the system comprises a staging module 51, for estimating the stage of the cancer, as further detailed hereinabove.

In various exemplary embodiments of the invention system 40 comprises a display device 54 which can display one or more of the clusters, as further detailed hereinabove. Display 54 can also display the biopsy locations, chemical element map, and/or additional biopsy location(s) on an image of the prostate, as further detailed hereinabove. Display 54 can also communicate with module 50 in which case display 54 can also display the estimated grade associated with one or more of the query clusters. Display device 54 can be a computer screen, a printing device, an image projector and the like.

As used herein the term "about" or "approximately" refers to ±10%.

The word "exemplary" is used herein to mean "serving as an example, instance or illustration." Any embodiment described as "exemplary" is not necessarily to be construed as preferred or advantageous over other embodiments and/or to exclude the incorporation of features from other embodiments.

The word "optionally" is used herein to mean "is provided in some embodiments and not provided in other embodiments." Any particular embodiment of the invention may include a plurality of "optional" features unless such features conflict.

The terms "comprises", "comprising", "includes", "including", "having" and their conjugates mean "including but not limited to".

The term "consisting of means "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

As used herein, the singular form "a", "an" and "the" include plural references unless the context clearly dictates otherwise. For example, the term "a compound" or "at least one compound" may include a plurality of compounds, including mixtures thereof.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

As used herein, the term "treating" includes abrogating, substantially inhibiting, slowing or reversing the progression of a condition, substantially ameliorating clinical or aesthetical symptoms of a condition or substantially preventing the appearance of clinical or aesthetical symptoms of a condition.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Various embodiments and aspects of the present invention as delineated hereinabove and as claimed in the claims section below find experimental support in the following examples.

EXAMPLES

Reference is now made to the following examples, which together with the above descriptions illustrate some embodiments of the invention in a non limiting fashion.

Materials and Experimental Methods

Example 1

Zinc Depletion, Gleason Scores and Lesion Size

X-Ray Fluorescence Measurements:

The methods and sample-handling protocols used in this study were described in details in PCT WO 2004/041060 to Breskin et al, filed Nov. 6, 2003, including details on calibration procedures and ways used to avoid sample drying during the measurements. Briefly, zinc concentration in the examined tissue-segments was quantified by X-ray fluorescence (XRF). Under the measuring conditions the sensitivity of both is about 20 counts per ppm, namely zinc concentration sensitivity better than 1 ppm. The calibration of both systems was checked against identical calibration standards, with absolute precision of a few µg/g (~1%). The reliability was checked by repeated measurements of the same sample, during the entire study, assessed to be within sigma=5%.

The measurements were carried out, in parallel, in two locations, using two tabletop XRF systems: one a locally-assembled system at the Kaplan Medical Center (KMC) and a commercial unit, custom-modified for our application, at the Sheba MC (SMC); the later system, with fully automated operation, had about 20 fold higher X-ray flux and superior spectrum quality. Both XRF systems were calibrated with the same calibration standards, permitting to combine data from the two experiments.

At KMC, 6 needle-biopsy samples (out of 12 extracted) per patient, each being a 0.5 mm in diameter and 15-20 mm long tissue cylinders folded in two, were placed between two 2.5 micron Mylar foils, on the sample tray that incorporated wet sponges. The sample tray was designed to minimize radiation scattering and to reduce sample drying (to <1%) during the 20-30 minutes measurement per patient. The sample tray was manually linearly-translated, introducing one sample at a time into the measurement site. The entire sample was irradiated and its average zinc content was calculated with a precision ranging from 30% to 5%, for 30 and 500 µg/g, respectively. At SMC, all extracted 8 needle-biopsy samples of same dimensions as above, were individually placed between two 2.5 microns Mylar foils in special cups, and mounted, tangentially aligned, on a rotating table. No drying was observed during the 12 minutes measurement per patient. The SMC XRF system afforded measurement of the zinc content within four different segments, each 5 mm long, along the sample; the zinc content precision was 15% to 5% for levels of 50 to 200 µg/g, respectively.

The clinical protocols were identical in both medical centers. The fresh needle-biopsy tissue cores were placed on their respective supports immediately after extraction, and introduced into the XRF system within minutes. Following the zinc measurement, the samples were marked (rectal end) and stored in formaldehyde for routine histological processing: embedding in paraffin wax, slicing into 4 micrometer thick slices, and staining with hematoxylin and eosin. Pathological examination results included a diagnosis including Gleason score and the % gland, namely the fraction of surface occupied by the glandular tissue. Diagnostic categories are: PCa (adenocarcinoma), BPH (benign prostatic hyperplasia), PIN (prostatic intraephytelial neoplasia), ASAP (atypical small acinar proliferation) or GRAN (granulomatous inflammation).

Data Correlations:

The present mode of analysis provides three levels of data: a segment zinc concentration and its corresponding histological classification; a core zinc concentration and its corresponding diagnosis and a patient average zinc concentration and its corresponding diagnosis. (The patient-average zinc is the average of measured zinc-concentration values over the entire volume of the extracted tissue per patient). A patient is defined as PCa one if any of his biopsy cores was diagnosed as PCa. A sample or a segment is defined as PCa only if the diagnosis of that sample or segment is PCa. All other diagnoses otherwise specified, are referred to as Non-Cancer.

Other relevant patient data from medical files, such as PSA, age, zinc-rich nutrition supplements, prostate size, etc, has also been collected and analyzed for correlation. The data analysis included correlation of different variables (e.g. zinc concentration) with the diagnosis, PSA, % gland, and other parameters from the patient's files; it also included the construction of sensitivity vs. specificity (Receiver Operating Characteristic=ROC) curves of some parameters or parameter combinations. PCa detection capability based on zinc mapping has been evaluated by computer simulation of zinc maps (using the measured data) with lesions of various sizes at random location, followed by image analysis and derivation of the respective ROC curves.

Grading of Tissue Samples:

Tumors are labelled according to pathological grade classification as "well-", "moderately-", and "poorly-" differentiated, corresponding to Gleason-score values of 5-6, 7 and 8-10, respectively. The Gleason score relies on the topology of cancer cells in the gland; it evaluates their resemblance or difference to normal-gland topology and consequently describes the aggressiveness of the lesion. The Gleason score and grade scale are described in detail hereinbelow.

Gleason Score and Prostate Cancer:

The histological grade, also called pathologic grade, is an important predictive factor of malignant disease, and is commonly used to define the potential for local and/or distant progression of malignant tumours. Not all prostate carcinoma progress along the same path: the majority of PCa cases are indolent with non-clinical manifestation; in other cases, the disease is localized, well confined to the prostate, with very slow progression; other carcinomas, with metastatic potential, evolve rapidly to a life-threatening disease. The rapidity and path of the carcinoma development depend on how closely the cancerous cells resemble normal ones.

The most accepted histopathological grading system is the one proposed by Donald F. Gleason, which is presently the most practiced prognostic factor, being significantly associated with survival and/or progression of the PCa. The Gleason-grade scale is based on the histological pattern of differentiation and arrangement of carcinoma in hematoxylin-eosin (H&E)-stained sections (FIG. 1). Five patterns are identified, from grade 1, being the most well-differentiated cancer (slow-growing), to grade 5, being the most poorly-differentiated cancer (most aggressive and fast-growing). To take into account the large heterogeneity displayed by the prostate-carcinoma tissue, to each tumour a primary and a secondary grade are assigned, with respect to the most common pattern (>50% of the total cancer-lesion area) and the second most common one (<50%, but ≥5% of the total cancer-lesion area). The two values, between 1 and 5, are added to generate the histological Gleason score (also called Gleason sum score and combined Gleason grade), ranging from 2 to 10. As used herein, the term Gleason score is used to indicate the sum of the grades of the two most dominant patterns. Thus, although PCa of Gleason grade 3+4 (primary grade 3 and secondary grade 4) and PCa of Gleason grade 4+3 (primary grade 4 and secondary grade 3) have the same Gleason score, equal to 7, they are strictly different from a pathological point of view; and they may have different disease-free survival rates and different zinc-content frequency distributions.

It is a common practice to characterize the cancer both by the clinical stage (dimension and spread), and by the Gleason grade. Thus, updated classification based on Gleason grade defines as "well differentiated" a PCa of grade (3+3), as "moderately differentiated" the grades (3+4, 3+5, 4+3, 5+3), and as "poorly differentiated" the high Gleason grades (4+4/4+5/5+4/5+5).

Results

Age, Size and PSA Distributions

Data source (KMC or SMC) is identified on each graph or table.

Table 1 summarizes the total patient statistics. Table 2 summarizes the total tissue-segments statistics.

TABLE 1

Total patient statistics.

| MC | Total No of patients | Non-Cancer diagnosis | PCa diagnosis |
|---|---|---|---|
| Sheba | 272 (21) | 203 (17) | 69 (4) |
| Kaplan | 326 | 237 | 89 |

(Note:
Numbers in parentheses indicate the number of patients consuming zinc-rich dietary supplements.)

TABLE 2

Total statistics of 1 mm³ tissue segments.

| Total number of segments | Non-Cancer segments | PCa segments |
|---|---|---|
| 8992 (668) | 8323 (635) | 669 (33) |

(Note:
Numbers in parentheses indicate the number of patients consuming zinc-rich dietary supplements.)

Figure 2A:
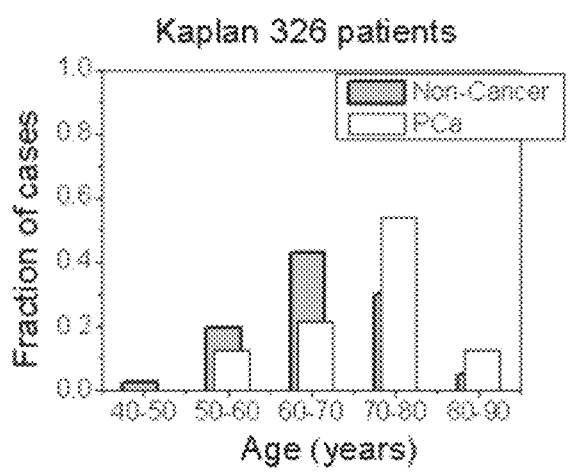
FIGS. 2A-B show age distributions (fraction of cases) of Non-Cancer and PCa patients undergoing TRNB examination in two medical centers: Kaplan medical center (KMC) and Sheba medical center (SMC).
Figure 2B:
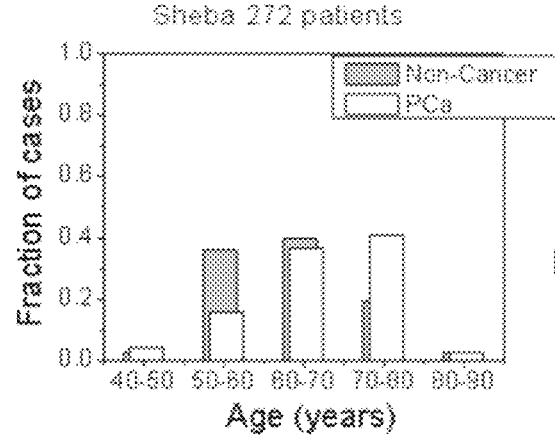
Figure 3A:
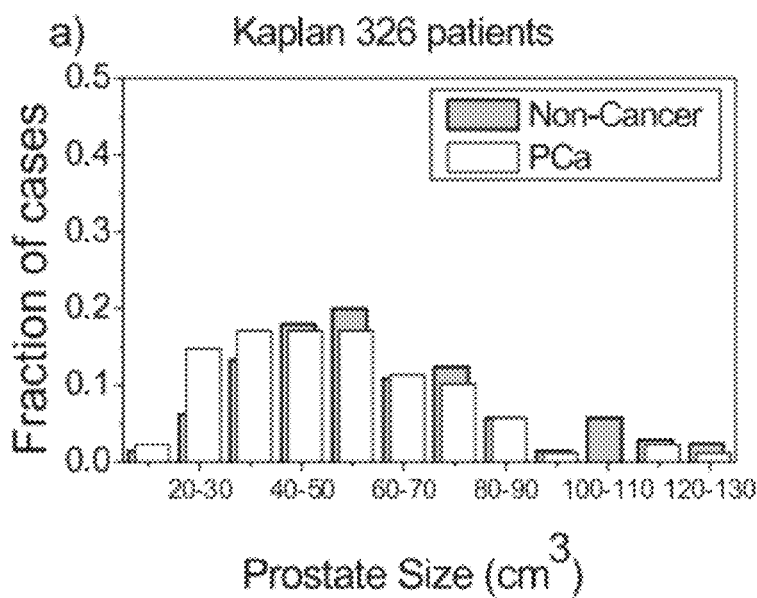
FIGS. 3A-B show prostate-volume distributions (fraction of cases) of Non-Cancer and PCa cases in KMC and SMC.
Figure 3B:
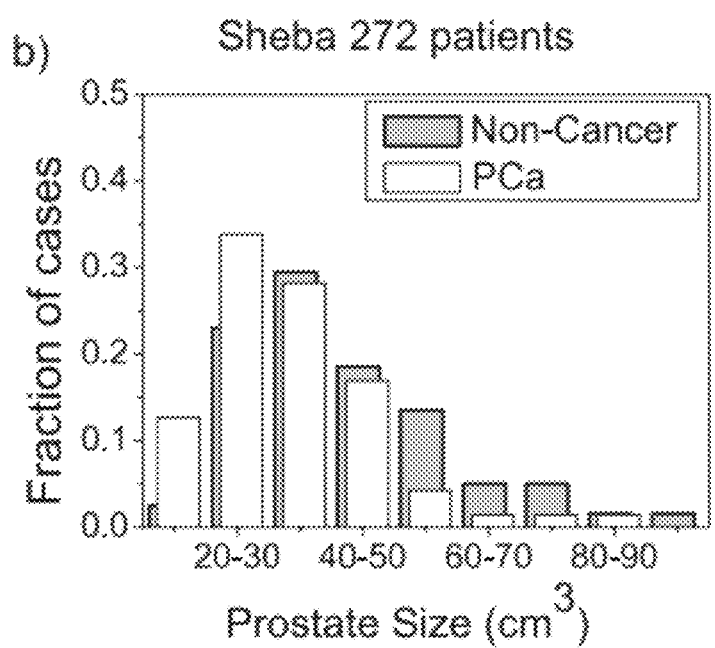
Figure 4A:
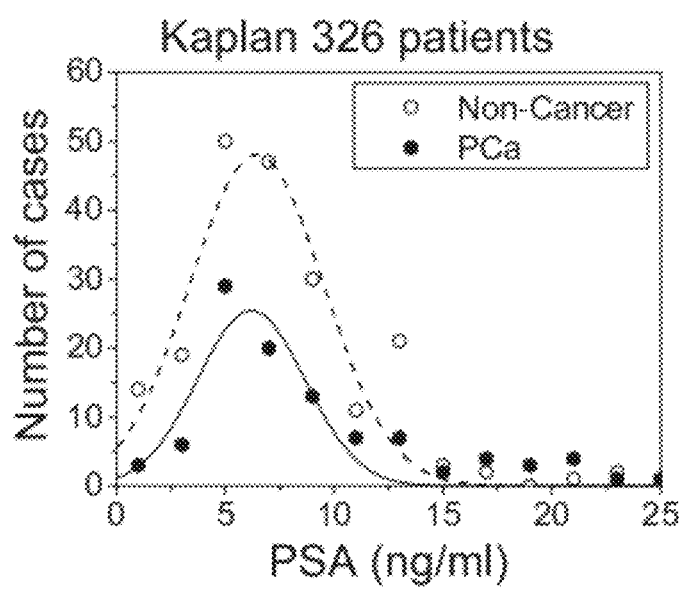
FIGS. 4A-B present PSA distributions for the same patient groups, together with normal curves fitting the data up to PSA=15.
Figure 4B:
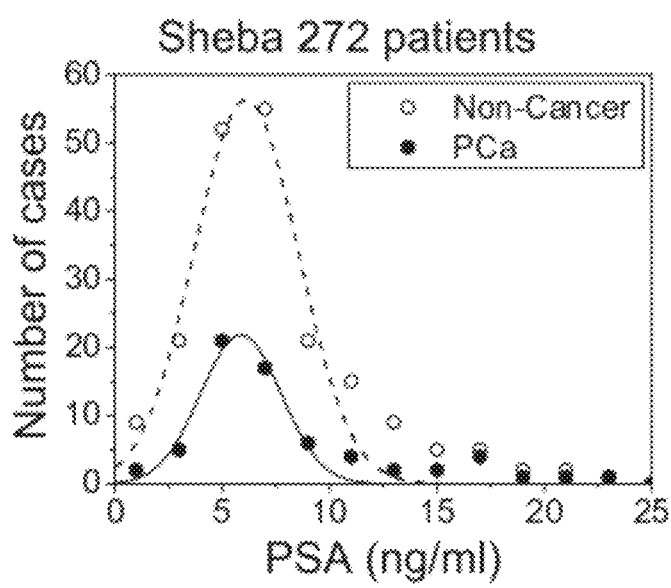
Figure 5:
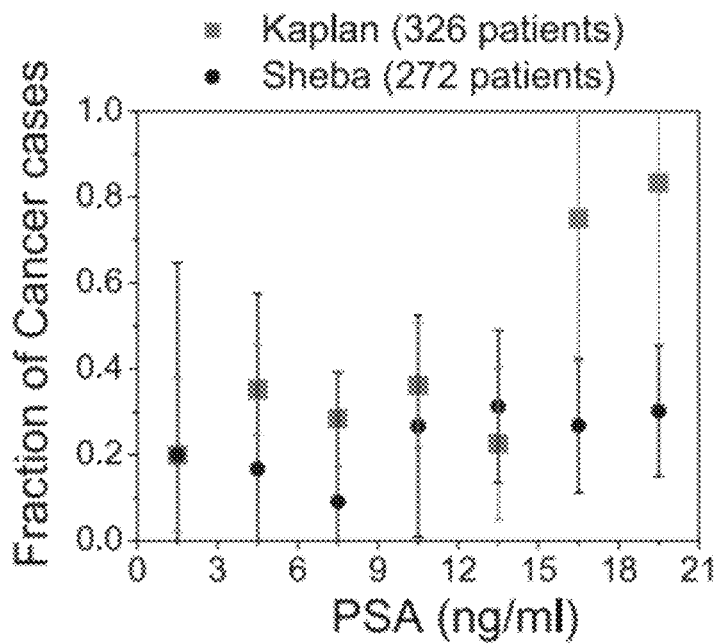
FIG. 5 presents the same data used in FIGS. 4A-B as fraction of PCa cases vs. PSA.

FIGS. 2A and 2B show the age distribution (fraction of cases) of Non-Cancer and PCa patients in the two facilities. Though SMC has relatively more cases in the age 50-60 and less in the age 70-80 groups, in both locations the PCa mean age (67 and 70 years, SMC and KMC, respectively) is higher than the Non-Cancer mean age (63 and 66 years SMC and KMC, respectively). FIGS. 3A and 3B depict the prostate-volume distribution (fraction of cases) of Non-Cancer and PCa cases in both locations; the distribution in KMC is broader. In both locations the mean volume for the PCa group (33 and 52 cm³ SMC and KMC, respectively) is smaller than that of the Non-Cancer group (42 and 60 cm³ SMC and KMC, respectively). Nevertheless, the shift in the respective distributions' mean values is small compared to their widths and they remain inseparable, even when age and size are combined. The PSA distributions for the same patient groups, together with normal curves fitting the data up to PSA=15, are presented in FIGS. 4A and 4B, showing very similar mean and width values for PCa and Non-Cancer in both medical centers. More interestingly, FIG. 5 presents the same data as fraction of PCa cases vs. PSA: this fraction is rather constant, at about 25%; for the KMC data there is not enough statistics above PSA of 15. FIGS. 4A, 4B and 5 together are consistent with the conclusion that PSA has no diagnostic value for those patients referred to the biopsy clinics. Using PSA derivatives, namely PSA normalized to the prostate volume (PSA density) and to patient's age, actually reflects the sensitivity of the diagnosis to age and size but not to PSA.

Figure 6:
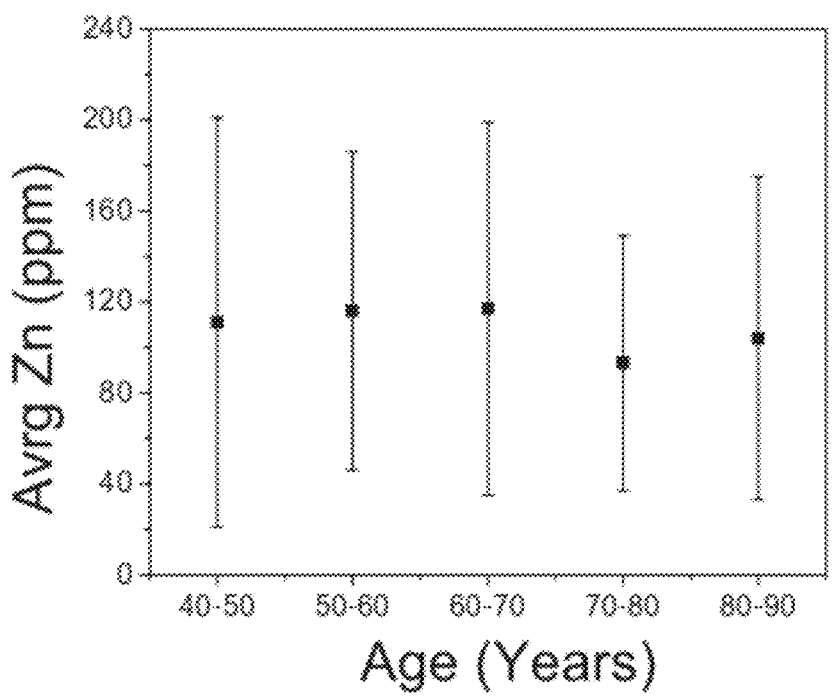
FIG. 6 shows the effect of patient age on the average zinc concentration in the prostate, based on 203 non-cancer patients at SMC.

The effect of patient age on the average zinc concentration in the prostate is depicted in FIG. 6, based on 203 non-cancer patients at SMC. For each age group zinc has a normal distribution with mean of ~110 and standard deviation of about 60 ppm. There is no evident age effect.

Zinc-Rich Nutrition Effects on Zinc Concentration Measurements

Figure 7A:
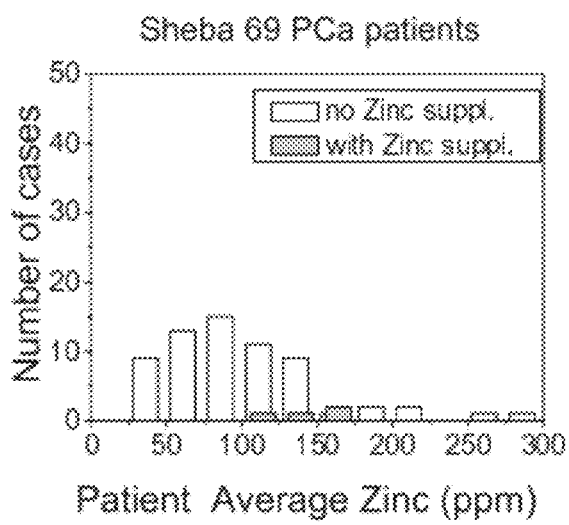
FIGS. 7A-7C present the patient-average zinc concentration for PCa- and Non-Cancer diagnosed patients, with and without zinc supplement in their diet.
Figure 7B:
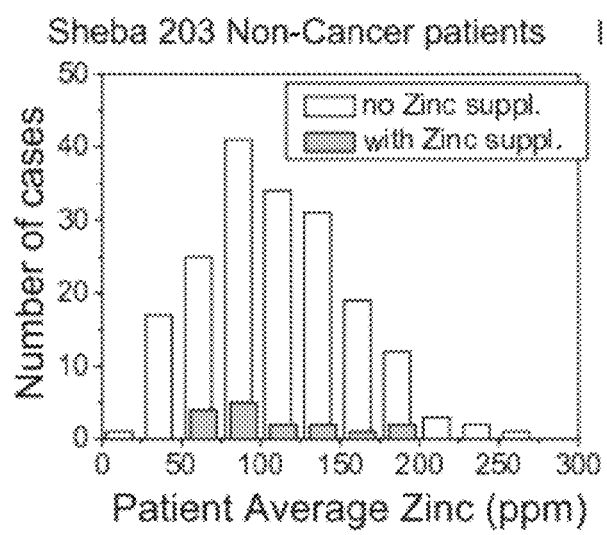
Figure 7C:
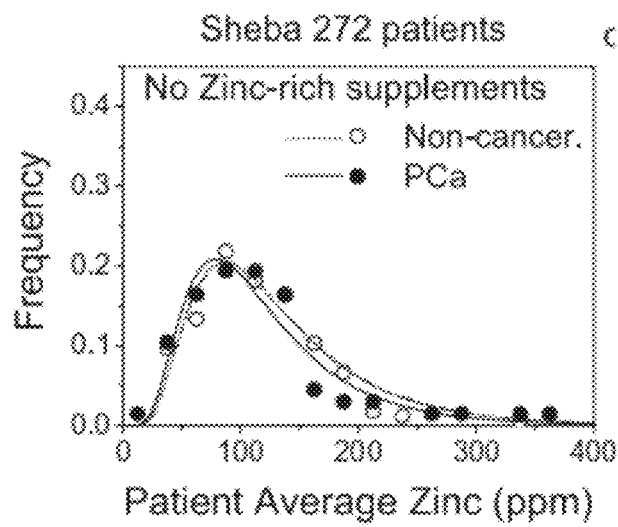

In order to assess the possibility of a falsely-elevated zinc concentration due to zinc-supplements consumption (e.g. multi-vitamins. See Table 1), the effect of zinc supplementation on the segment and on the patient-average data levels was examined. FIGS. 7A-7C present the patient-average zinc concentration for PCa- and Non-Cancer diagnosed patients, with and without zinc supplement in their diet. (see Table 1, above). Among the 69 PCa-diagnosed patients only 4 persons reported a zinc-rich diet; seemingly, their average zinc values are significantly different from that of the others, but the poor statistics do not afford accurate evaluation. Statistical Kolmogorov-Smirnov (K-S) test, with confidence 5%, confirms that, with regard to patient-average zinc concentrations, the two Non-Cancer populations and the PCa "no-zinc-supplement" population may all be considered identical. In other words, in the absence of zinc-rich diet, the patient-average zinc has identical distributions for both diagnoses (see FIG. 7C). In the presence of a zinc-rich diet, the results are rendered inconclusive, with an indication of further ambiguity of the diagnostic value.

Figure 8A:
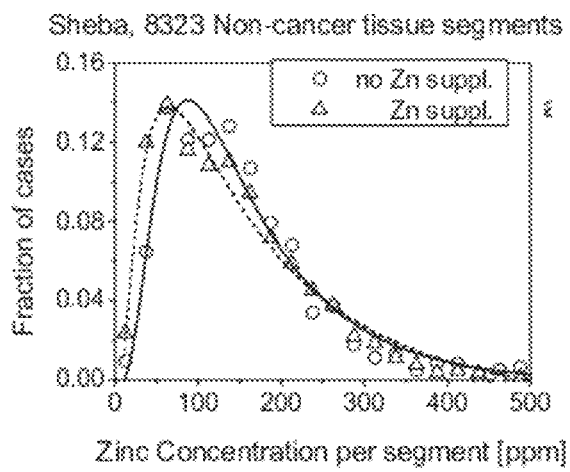
FIGS. 8A and 8B show zinc concentration distributions (Fraction of cases) measured within a 5 mm long biopsy segments (~1 mm$^3$ tissue), for PCa- and Non-cancer classified tissue segments, for patients with and without zinc-rich diet
Figure 8B:
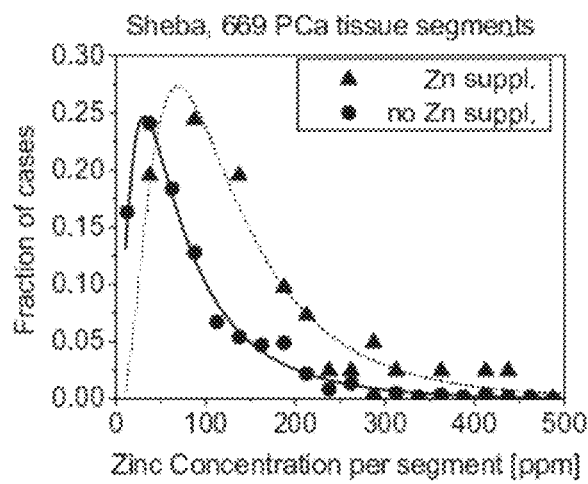

The results are clearer when studying the zinc-rich nutrition effect at the data level of tissue segments. FIGS. 8A and 8B show zinc concentration distributions (Fraction of cases) measured within a 5 mm long biopsy segments (~1 mm³ tissue), for PCa- and Non-cancer classified tissue segments, for patients with and without zinc-rich diet. The data was fitted with lognormal curve (the variable's logarithm is normally distributed $$f(x; \mu, \sigma) = \frac{\exp[-(\ln x - \mu)^2/(2\sigma^2)]}{x\sigma\sqrt{2\pi}} \text{ for } x > 0,$$

where $\mu$ and $\sigma$ are the mean and standard deviation of the variable's logarithm), and analyzed with K-S test to compare the distributions of different ensembles. The zinc-rich diet does not affect the distribution's width but it does shift its mean. The shift is negative (from 109 to 103 ppm) for Non-Cancer tissue segments, and statistically significant; it is more pronounced and positive (from 56 to 81), and statistically significant, in the PCa tissue segments. More importantly, the Non-Cancer "no-zinc-supplement" distribution and the PCa with zinc supplement distribution are not statistically different, clearly demonstrating the obscuring effect of zinc-rich dietary components.

Figure 9:
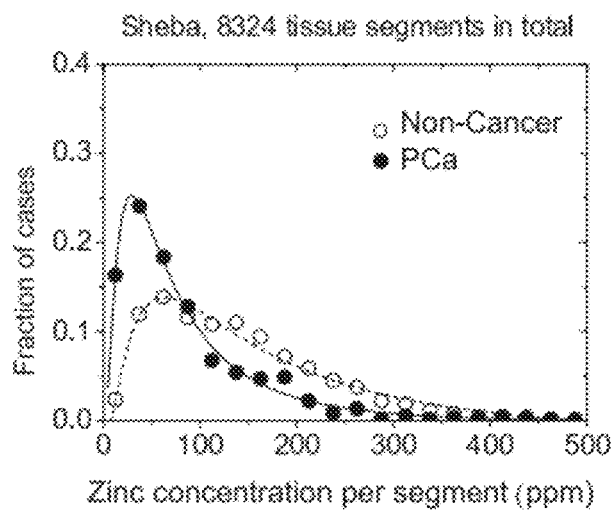
FIG. 9 shows a comparison of zinc concentration distributions (fraction of cases) of tissue segments diagnosed Non-Cancer or PCa (n total=8324 segments), from patients not on a zinc-rich diet.

On the other hand, the local zinc concentration (FIG. 9) in the absence of zinc-rich diet has distinctly different distributions for tissue segments classified as PCa or Non-Cancer, with their mean ($\mu$) shifted by a factor of 1.44 and their respective standard deviation ($\sigma$) by factor 0.96. This shift ratio is smaller than the one reported in the literature regarding patients having advanced disease. Nevertheless, the shift between the two distributions represents a confirmed diagnostic value attributed to the zinc concentration measured in 1 mm³ segments. It is also evident that the diagnostic value is degraded in patients subject to zinc-rich diet.

Based on these findings, data from patients consuming zinc-rich nutrition supplements was excluded from the statistical analysis. The effect of this exclusion on the conclusiveness of the results was deemed negligible.

Zinc Concentration in PCa Patients—Correlation with Gleason Score

In order to determine whether zinc concentration can be used for staging PCa, zinc-concentration in PCa-diagnosed patients confirmed to avoid zinc-rich diet, and its correlation with the Gleason score was measured. The correlation is presented for patient average, core data level and segment data level. In almost all cases the Gleason score values assigned to all the malignant segments of a given patient were identical, and equal to the Gleason score assigned to the patient. Therefore, Non-Cancer tissue was also classified according to the Gleason score of the patient. Table 3 below provides the information on PCa-patients number per each Gleason score category (65 in total); the well-, moderately- and poorly-differentiated categories correspond to Gleason score values of 5-6, 7 and 8-9. This grouping was needed due to the low statistics. The 7 patients diagnosed for minimal volume carcinoma (MVC) were considered separately. Table 3 also summarises the statistics of tissue cores and tissue segments classified in the same way.

TABLE 3

The number of PCa-diagnosed patients and of cancerous and Non-Cancer tissue cores and tissue segments, classified according to the various Gleason score categories.

| | Min. volume carcinoma | Well differentiated Gleason score 5-6 | Moderately differentiated Gleason score 7 | Poorly differentiated Gleason score 8-9 |
|---|---|---|---|---|
| PCa patients | 7 | 36 | 22 | 11 |
| Non-Cancer cores | 38 | 192 | 86 | 14 |
| PCa cores | 55 | 84 | 99 | 55 |
| Non-Cancer segments | 180 | 896 | 462 | 100 |
| PCa segments | 26 | 177 | 246 | 166 |

Note:
MVC = minimal volume carcinoma which is considered separately. Data from SMC.

Figure 10A:
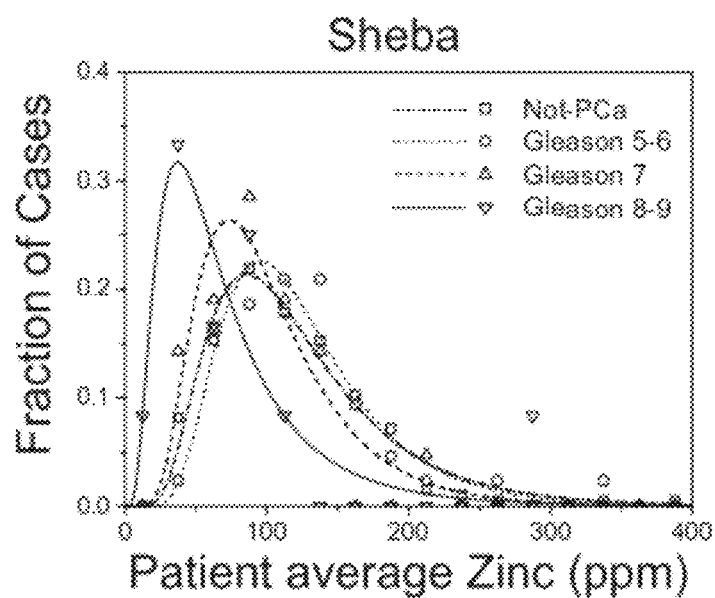
FIGS. 10A-B show distributions of patient-average zinc concentration (Fraction of cases) for cancer patients at SMC and KMC, according to their Gleason score.
Figure 10B:
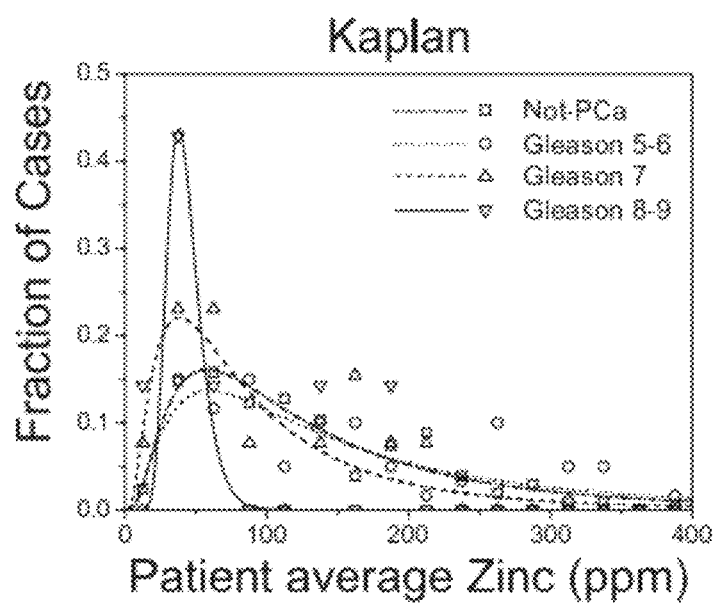

FIGS. 10A and 10B shows the distributions of patient-average zinc concentration (Fraction of cases) for cancer patients at SMC and KMC, according to their Gleason score; the non-cancer patients' distribution is given for comparison. Kolmogorov-Smirnov test confirmed that the non-cancer and the Gleason <8 groups are statistically identical. The Gleason 8-9 group seems to be significantly different but it has low statistics and the test is inconclusive.

Figure 11A:
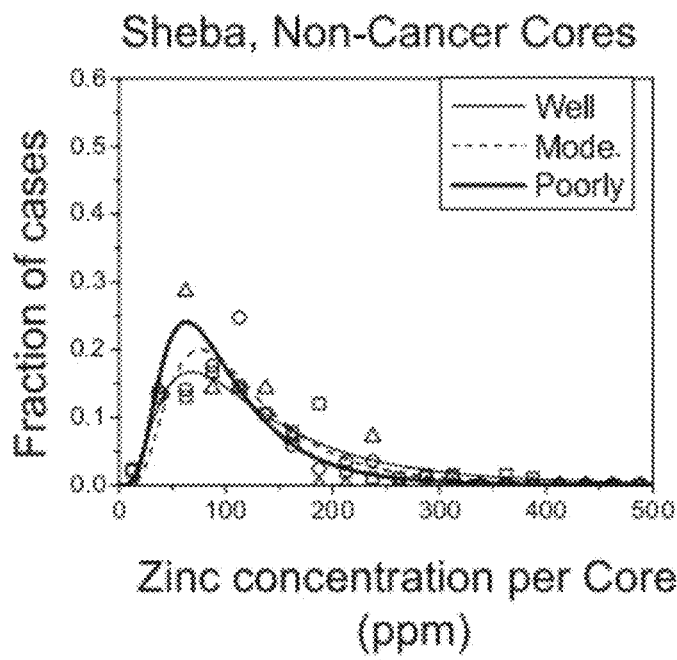
FIGS. 11A-B shows zinc concentrations of all (cancerous and non-cancerous) biopsy cores (4 mm$^3$ tissue), from PCa-diagnosed patients, plotted as a fraction of cases and fitted with lognormal functions.
Figure 11B:
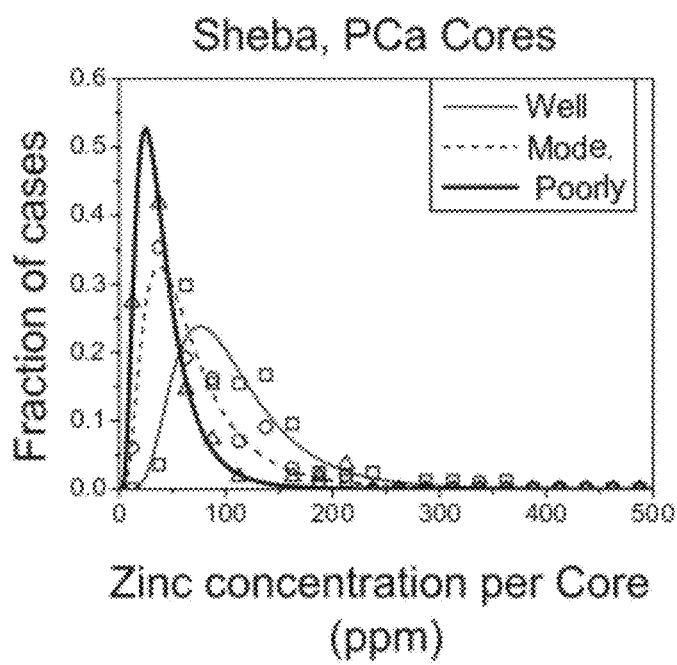

FIGS. 11A and 11B shows zinc concentrations of all (cancerous and non-cancerous) biopsy cores (4 mm$^3$ tissue), from PCa-diagnosed patients, plotted as a fraction of cases and fitted with lognormal functions. The shift in the geometrical mean is small (10% between the categories) for the Non-Cancer cores, but very pronounced (factors 1.7 and 2.7) for the PCa cores. In accordance with the shift of the mean, the distribution width becomes smaller with increasing Gleason score. Checking the contrast between Non-cancer and PCa, a K-S test (run at confidence level 5%) confirmed that for the moderately and poorly differentiated PCa, the zinc-value groups are statistically different from the Non-Cancer group, while the two zinc value groups of the well differentiated PCa and Non-Cancer groups are statistically identical populations.

Figure 12A:
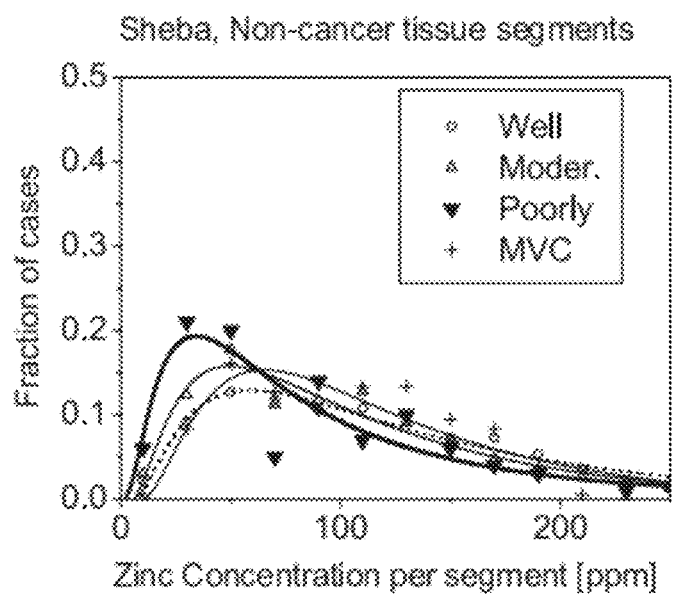
FIGS. 12A-B show zinc concentration distributions (plotted as fraction of cases) of all (non-cancerous and cancerous) tissue segments (1 mm$^3$) from PCa diagnosed patients, fitted with lognormal functions, for the non-Cancer (FIG. 12A) and the PCa (FIG. 12B) tissue segments, as function of Gleason score category.
Figure 12B:
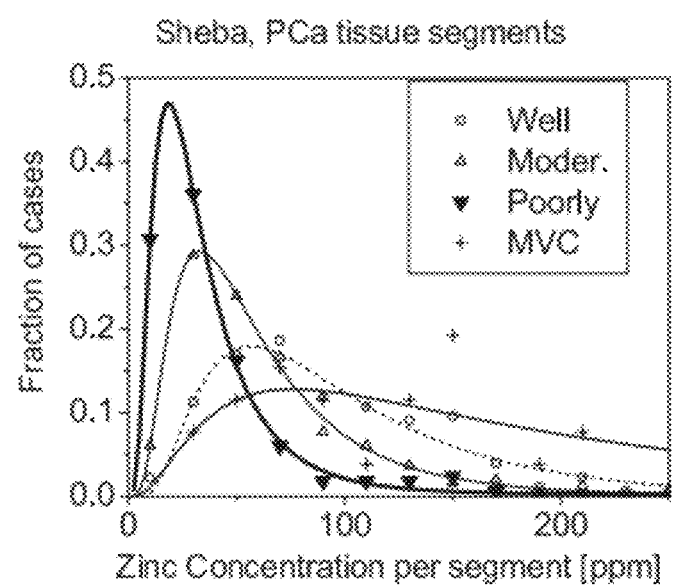
Figure 13A:
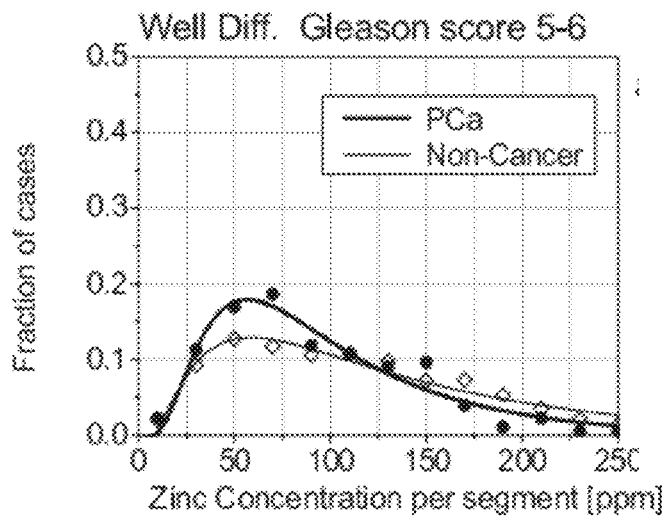
FIGS. 13A-C show zinc concentration distributions for non-cancer and PCa tissue segments, and their respective fits, for each Gleason score category (well differentiated in FIG. 13A, moderately differentiated in FIG. 13B, and poorly differentiated in FIG. 13C).
Figure 13B:
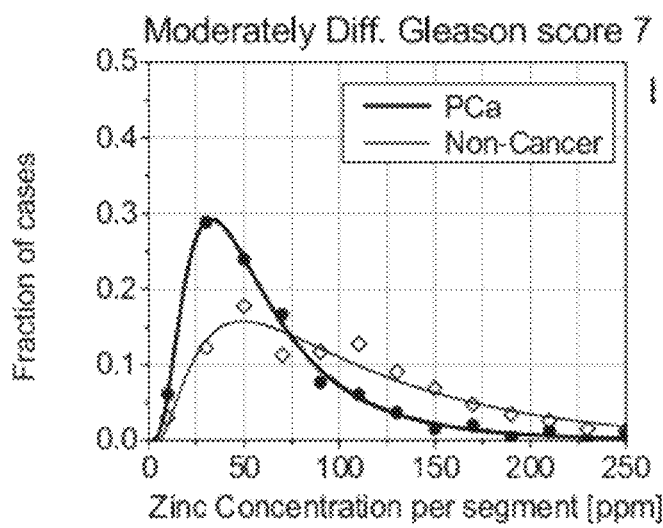
Figure 13C:
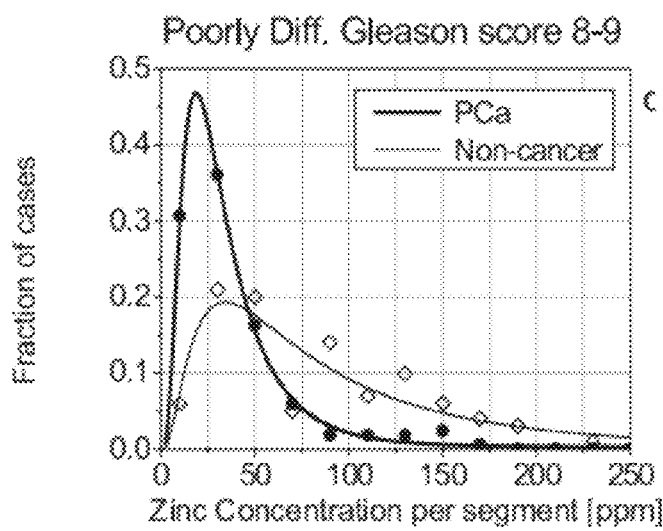

FIGS. 12A and 12B show zinc concentration distributions (plotted as fraction of cases) of all (non-cancerous and cancerous) tissue segments (1 mm$^3$) from PCa diagnosed patients, fitted with lognormal functions, for the Non-Cancer (12A) and the PCa (12B) tissue segments, as function of Gleason score category. A very pronounced systematic shift to lower zinc values with increasing Gleason score is observed for the cancerous tissue, while a much more moderate shift exists in the Non-Cancer component. (The distribution in Non-Cancer tissue segments from Gleason score 5-6 patients is practically identical with that found in non-cancer patients). As a result, the contrast between cancer and non-cancer zinc levels increases with Gleason score. This is demonstrated in FIGS. 13A-13C, which show the zinc concentration distributions for Non-Cancer and PCa tissue segments, and their respective fits, for each Gleason score category (13A=Well differentiated; 13B=Moderately differentiated; and 13C=Poorly differentiated). While for low Gleason score (well differentiated cancer, FIG. 13A) the peaks of Non-Cancer and cancer tissue are shifted by only 30%, and their widths are very similar, the separation becomes more pronounced with increasing Gleason score; for high Gleason score (poorly differentiated cancer, FIG. 13C) the distributions mean values ($\mu$) differ by a factor of 2.6, and their respective standard deviation ($\sigma$) by a factor 0.8.

Evaluation of the Diagnostic Value of Zinc Concentration

Figure 14:
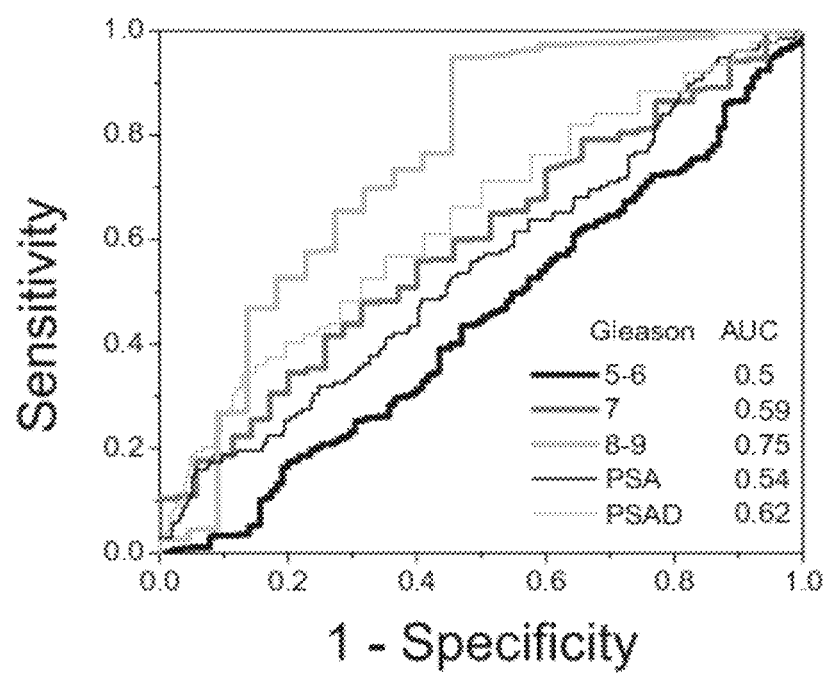
FIG. 14 shows an ROC curve of zinc concentration averaged over the entire volume of the extracted tissue (patient average). AUC=area under the curve.

The diagnostic value of zinc concentration averaged over the entire volume of the extracted tissue (patient average) may be evaluated from the sensitivity versus specificity curve (ROC curve, or True Positives rate versus False Positives rate) of this parameter (FIG. 14). The diagnostic value (area under the curve, or AUC) improves with the Gleason score. The ROC for PSA and PSAD (PSA density) in our patients' population is given for comparison. Note that the patient-average zinc concentration has a better AUC only for the highest Gleason score, 8-9. (to improve the statistical significance of Gleason 8-9, the data from both KMC and SMC was combined in this case).

In order to evaluate the diagnostic value of the local (e.g. segments) zinc concentration, a large number of data points per patient (up to 32 in our case) can be converted into a single value, for which a sensitivity versus specificity (ROC) curve could be constructed, thereby permitting comparison of the quality of zinc concentration diagnosis with other existing indicators such as PSA and its derivatives.

Figure 15A:
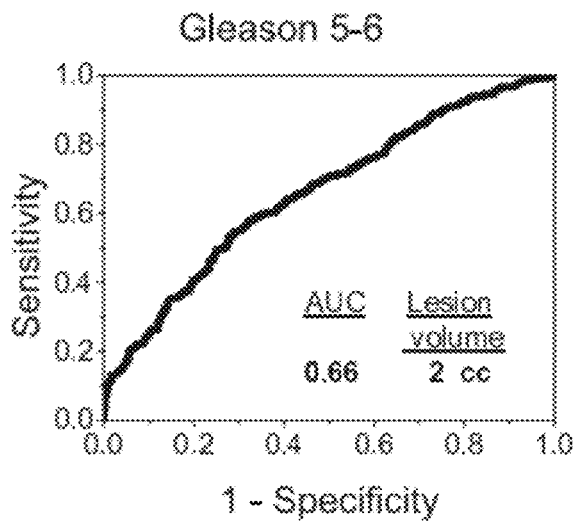
FIGS. 15A-C show ROC curves based on simulated lesions of various dimensions and Gleason scores, using the data of FIG. 13. AUC=area under the curve.
Figure 15B:
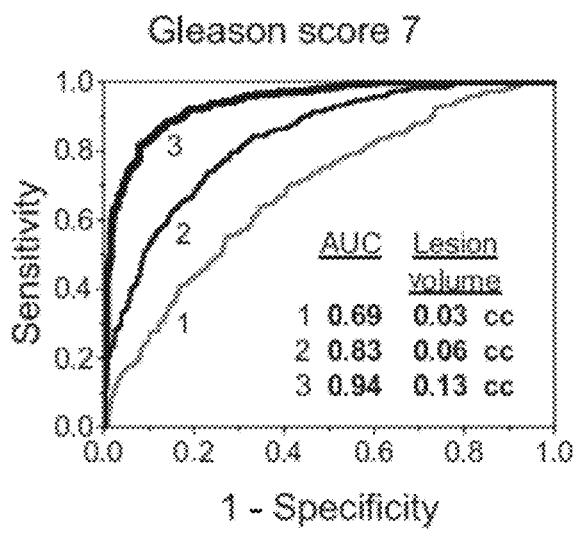
Figure 15C:
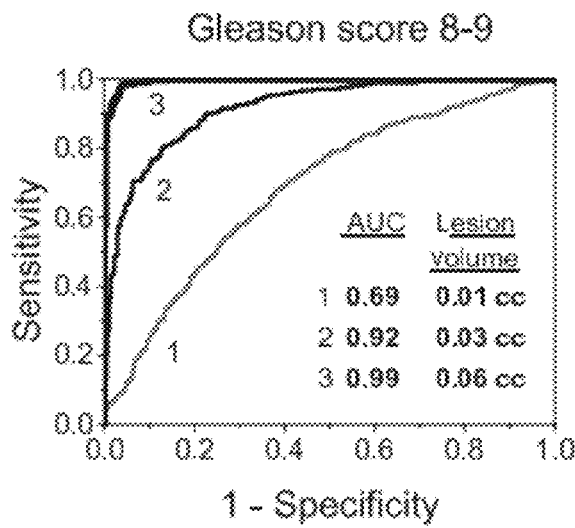

Alternatively, the diagnostic value of zinc-concentration information can be assessed by assuming that a full zinc-concentration map (two or three dimensional) could be produced, and then confirming the diagnostic value of such a map. In order to evaluate the usefulness of such data, maps have been produced by computer simulations, using the measured zinc-concentration data of FIGS. 12A and 12B as input. "Lesions" of various sizes and Gleason score were deposited at random locations within the maps, and a simple pattern-recognition procedure was used to identify local zinc depletion in the maps. (Optimum number of pixels per map and best possible pattern-recognition procedures are detailed herein). Representative ROC curves for each lesion size and Gleason score from this simulation study are depicted in FIGS. 15A-15C, showing ROC curves as function of lesion size and Gleason score. Detailed description of the data shown in FIGS. 15A-15C is provided hereinbelow. The curves of FIGS. 15A-15C indicate that, using a two-dimensional zinc-concentration map, very small lesions (about 0.1 cubic cm) of Gleason score 7 and up are expected to be detected with very high confidence. For comparison the ROC curves for PSA and PSA-density (PSAD) in our patients' population is also provided (FIG. 14). Clearly the AUC of the zinc-concentration based ROC curves are superior to those generated by PSA and PSAD data.

Taken together, these results clearly indicate that the local zinc level, measured in 1-4 mm$^3$ fresh tissue segments, shows a clear correlation with the histological classification of the tissue, whether Non-Cancer or malignant, and a systematic positive correlation with the Gleason score classification of the cancer: the higher the Gleason score the more zinc is depleted, and the greater the contrast between the malignant and the Non-Cancer tissue components. This indicates that the amount of zinc depletion could be used as a measure of the Gleason score of the tumor. Further, this indicates that the higher the Gleason score, the smaller the detectable lesion. In particular, measurement of patient-average zinc according to some embodiments of the present invention was found to be correlated with the disease grade and of greatest significance for lesions having high Gleason scores, of 8-9. Further, measurement of patient average-zinc according to some embodiments of the present invention was found to be diagnostically significant for low Gleason grade lesions measuring ~0.5 cm$^3$, and higher Gleason grade lesions, measuring ~0.1 cm$^3$.

Further, positive correlation of the local zinc concentration with the histological classification of the tissue, as Non-Cancer or PCa, with further correlation with the Gleason score within the PCa group is demonstrated, indicating that the specificity and sensitivity of local zinc concentration is highest for lesions with higher Gleason grade, of clinical importance.

Significantly, it was uncovered that the zinc depletion occurs not only in the cancerous tissue segments but also, though less pronouncedly, in the Non-Cancer components surrounding the lesion, and in correlation with the Gleason score, which may indicate that zinc depletion is an early step in the cancer proliferation process and that zinc depletion precedes the transformation of cells from normal to cancerous type. Thus, although PCa may not be histologically detectable in such regions, the cellular precursor for its appearance may already be present and active, and is more pronounced the more aggressive is the malignant process in the other parts of the prostate. Such pre-malignant and malignant processes in the peripheral zone may be detectable by measurement of zinc depletion.

Example II

Zinc Concentration Maps

In addition to detection and grading of cancerous and pre-cancerous foci, it would be highly desirable to have tools for accurate and non-invasive location and imaging of prostate lesions, in order to detect both location, dimension and grade of lesions. In order to test whether zinc depletion data generated in accordance with some embodiments of the instant invention, can be useful in location and imaging of prostate lesions, zinc-concentration maps were generated from experimental zinc-concentration data. The maps represent prostate-tissue with lesions of different dimensions and histological grades, at various locations within the gland. The maps are then transformed into 8-bit images and processed with a simple image processing algorithm yielding a one-parameter classifier test.

Generation of Zinc Concentration Maps

Figure 16:
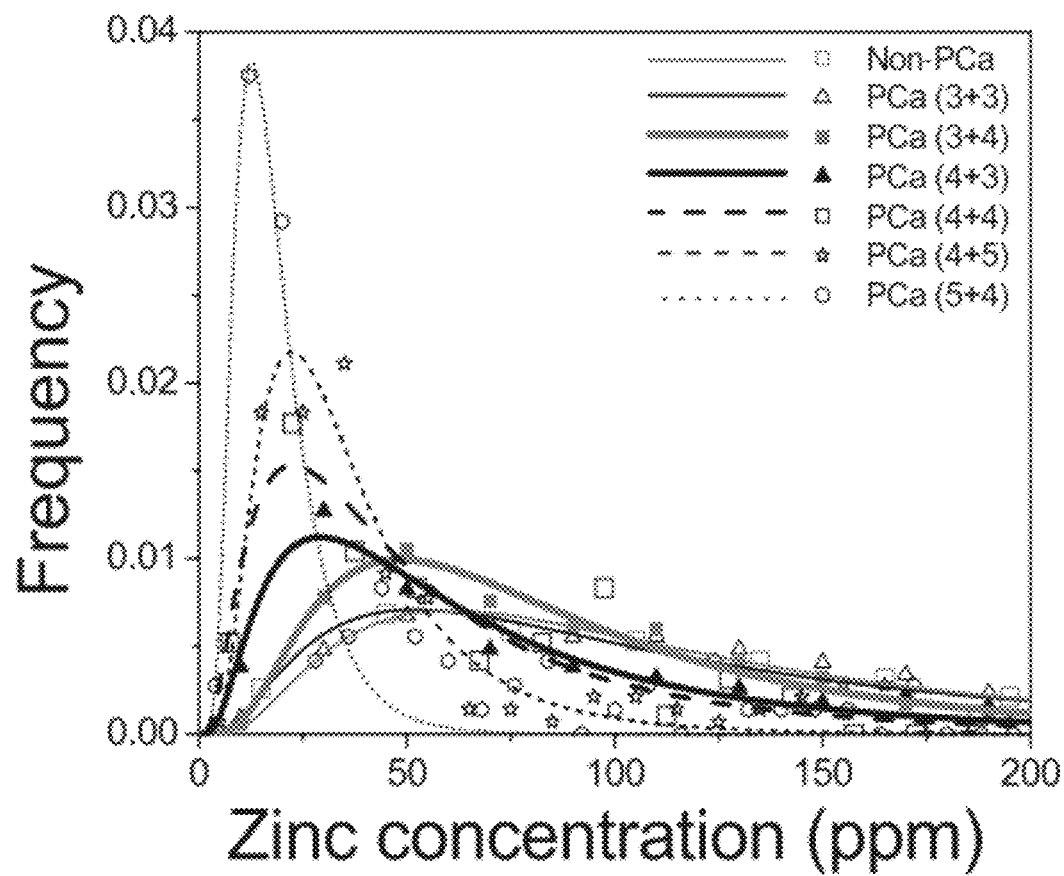
FIG. 16 shows a representative frequency distribution of zinc-concentration for PCa tissue segments of 1 mm$^3$, classified according to the Gleason scores of 6 to 9, representing Gleason grades of (3+3) to (5+4), as well as frequency distribution of zinc-concentration in the non-PCa tissue component, in segments of same size.

FIG. 16 shows a representative frequency distribution of zinc-concentration for PCa tissue, based on the data presented in FIGS. 12A and 12B, classified according to the Gleason scores of 6 to 9, representing Gleason grades of (3+3) to (5+4), as well as frequency distribution of zinc-concentration in the non-PCa tissue component.

Note that all the zinc distributions in FIG. 16 appear to be strongly asymmetric, a feature usually attributed to frequency distribution of non-essential trace elements. In addition, the asymmetry is statistically more significant at larger cancer grades; i.e. higher Gleason-grade, with a sizable increase of the distribution skewness towards lower zinc values. All the frequency distributions were fitted with lognormal functions.

Two-dimensional zinc-concentration maps, representing 1 mm thick prostatic tissue layers of area 3×3 cm$^2$, with or without cancerous lesion, were generated using Monte Carlo tools. The experimental zinc distributions according to the measurements as shown in Example I, hereinabove (summarized in FIG. 16) were used as underlying sources of probability-distribution functions. The zinc-maps were defined as matrices of a given pixel-size, namely 10×10, 15×15, 20×20 and 30×30 pixels. Lesions were assigned certain Gleason grades and dimensions, a random location was assigned on the map and on an independent pixel basis, a zinc-level value assigned to each pixel in the map. This zinc-concentration value was defined by an appropriate random-number generator, from the corresponding lognormal distributions of FIG. 16, according to the assumed tissue classification of that pixel (FIG. 17). Optionally, the value could be modified at this point to include fluctuations originating from counting statistics, namely from the fact that the matrix is generated by a real detector.

In the next step, the pixels' content was quantized into 8-bit gray-scale by a process of colour quantization, with the gray-scale brightness ranging from 0 to 255; this created a concentration-scale of 2 ppm zinc-concentration steps, with the full-scale spanning the range of 0 to 510 ppm zinc. The map-generation algorithm and the succeeding image analysis were written with MatLab 7.0 (R14) software tools (The Math-Works Inc., Natick, Mass., USA).

Analysis of Zinc Concentration Maps

The analysis of the 8-bit images consisted of the following stages (i) Denoising (ii) Detection and Localization (iii) Classification and (iv) Grading In the very first step, the image is processed with a median filter, which led to high degree of noise reduction (Denoising) but preserved the edges of the image features. This is critical to the clinical application of such an imaging tool. In the second step, an automatic detection of local zinc-depleted features in the image was performed by an image-segmentation process, based on cluster-analysis. Image-segmentation is a low-level image-processing task that aims at partitioning an image into multiple chromatically-homogeneous regions. In recent years, many methods for improving segmentation-algorithm performance have become available, such as, for example, thresholding, clustering, or Markov random filed, etc.

Expectation-maximization (EM) technique for image segmentation was used for the analysis of zinc concentration data: EM is a well-known unsupervised clustering algorithm, which iteratively alternates between segmenting the image into N pixels' classes (clusters) and characterizing the properties of each class. The output image of the EM clustering algorithm (segmented image) represents a statistical description of the N clusters, providing the number of components in each cluster, localization of the cluster within the map, average grey-level and related variances associated to the cluster. Using this method, the digitized zinc-images are partitioned into 6 homogeneous clusters classified by their average grey-levels; however, only the cluster with the lowest grey-level value is identified as "suspected" cancer-lesion areas (Detection and Localization).

Figure 18A:
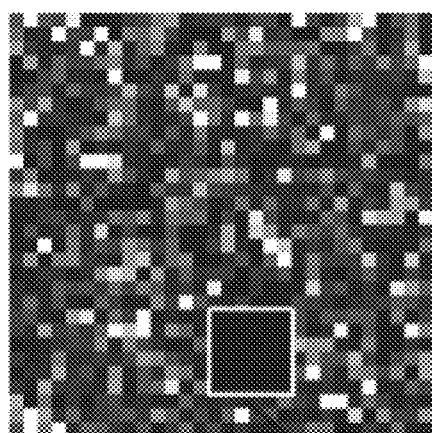
FIG. 18A shows a computer-simulated raw zinc image, as prepared according to various exemplary embodiments of the present invention.
Figure 18B:
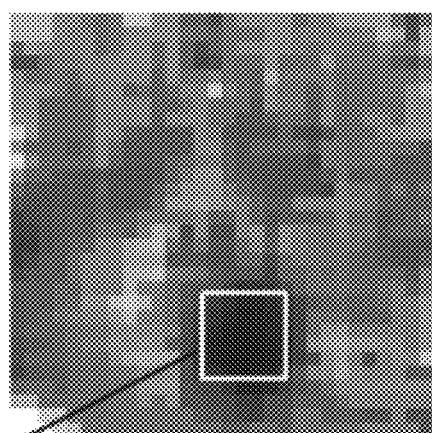
FIG. 18B shows the image of FIG. 18A after denoising process, according to various exemplary embodiments of the present invention.
Figure 18C:
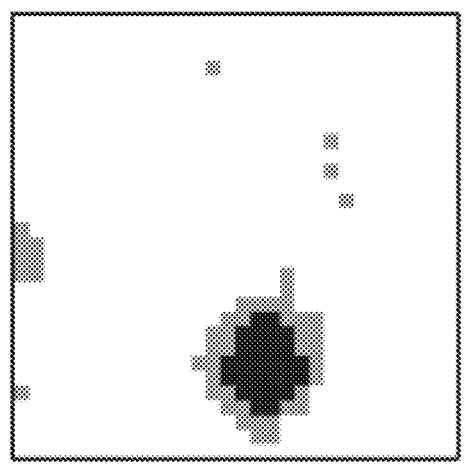
FIG. 18C shows the two clusters with lowest grey-level values after employing a clustering procedure to the image of FIG. 18B, according to various exemplary embodiments of the present invention. $LC_{Zn}$ is the average zinc concentration in the lowest grey-level cluster, calculated according to various exemplary embodiments of the present invention.

In FIG. 18C, only the two clusters with lowest grey-level value are shown, for better visualization of the cancer lesion in the classified image. The black area represents the lowest zinc cluster (detected cancer) while the contour grey area represents the second lowest zinc cluster (zinc depleted area). FIGS. 18A-18C show an example of zinc map and image processing results of 30×30 pixels, in which a 6×6 pixels lesion of Gleason grades 5+4 is randomly generated.

FIG. 18A shows the computer-simulated raw image while FIG. 18B shows the same image after denoising process: the gray-level patterns in the processed images correspond to the assumed zinc-level patterns, with the zinc depletion clearly visible among high zinc tissue background. In both FIGS. 18A and 18B, the computer-simulated cancer lesion, embedded in the non-cancerous-tissue background, is highlighted. Finally, FIG. 18C shows the result of image segmentation applied to the process computer-simulated map. The lowest grey-level cluster is drawn in black while the second-lowest grey-level clusters are in grey; white area represents benign tissue. The average values of the distribution of zinc in the lowest zinc cluster ($LC_{Zn}$) are also indicated.

Once the lowest-zinc cluster has been geometrically localized by image segmentation, the cluster needs to be classified as cancerous or non-cancerous (Classification) and, whenever it is classified as cancerous, it needs to be classified according its cancer-aggressiveness grade (Grading). Further, a stage can be assigned to the lesion, according to the size of the lesion detected in imaging.

The processes of classification and grading are performed by a single-parameter classification test, based on $LC_{Zn}$ values. The performance of the classifier test was computed and evaluated by means of Receiver Operating Characteristic (ROC) analysis. The ROC curve is a two-dimensional graph in which a true-positive rate (sensitivity) is plotted versus the false-positive one (1-specificity) for each classifier's cut-off value, the so called ROC space. An ideal binary classifier test would yield a step-function shape (0,1) in the ROC space, representing a sensitivity of 100% (all true-positives found) and 100% specificity (no false-positives found). The area under the ROC curve (AUC) is a common way of depicting the classifier-test quality and comparing the performances of classifiers and their combinations. An AUC close to 1 corresponds to an excellent diagnostic test while an AUC of 0.5 corresponds to a completely random one.

Several sets, each of 10,000 synthetic maps, with and without "lesions", were generated. The different sets were characterized by different image- and lesion-parameters, namely spatial resolution (total number of pixels), cancer-lesion size, Gleason grade. The relation between cancer detection performance and various image-parameters were evaluated, based on the image processing and ROC analysis detailed above, using the $LC_{Zn}$ value as test classifier. For each set of lesion- and map-parameters, images (with and without lesion) were generated and processed. The presence and location of an identified cancer were then compared to the input information. Consequently each missed or identified lesion could be tagged as true/false positive or true/false negative. The process was carried out while varying the threshold of the classifier test, to construct the entire relevant ROC curves.

Results

Prostate-Cancer Detection and Grading

According to current general practice, only tumours larger than 0.5 cm³ (about one fifth of the PCa tumours detected in autopsies) are considered to be of clinical significance, with further refinement claiming that tumour volume adjusted for grade is the appropriate predictor of disease-specific survival. Malignancies with a volume of 0.5 cm³ or less and a Gleason score of less than 7, are declared clinically-insignificant and may be managed by watchful waiting. Thus, within the present study clinically-relevant tumour-sizes were defined as above 0.5 cm³ for the more aggressive prostate cancers (above or equal to Gleason grade 4+4) and above 1 cm³ for the less aggressive ones (below Gleason grade 4+4).

The Effect of Pixel-Size/Density and Tumour-Grade on PCa Detection

Figure 19A:
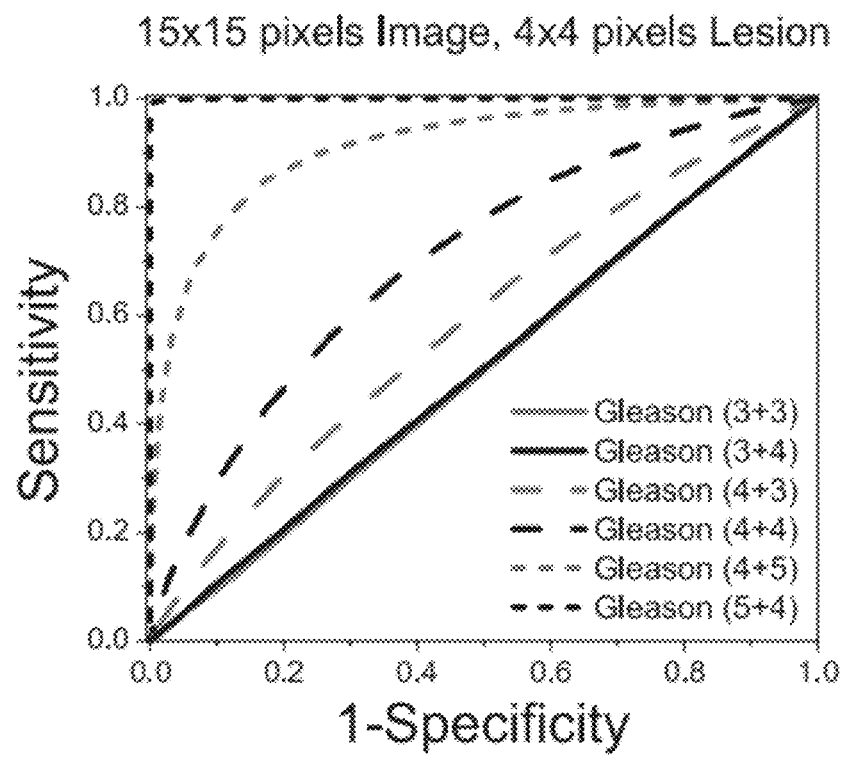
FIGS. 19A-B show ROC curves based on the analysis of zinc maps representing 3×3 cm² prostate sections.
Figure 19B:
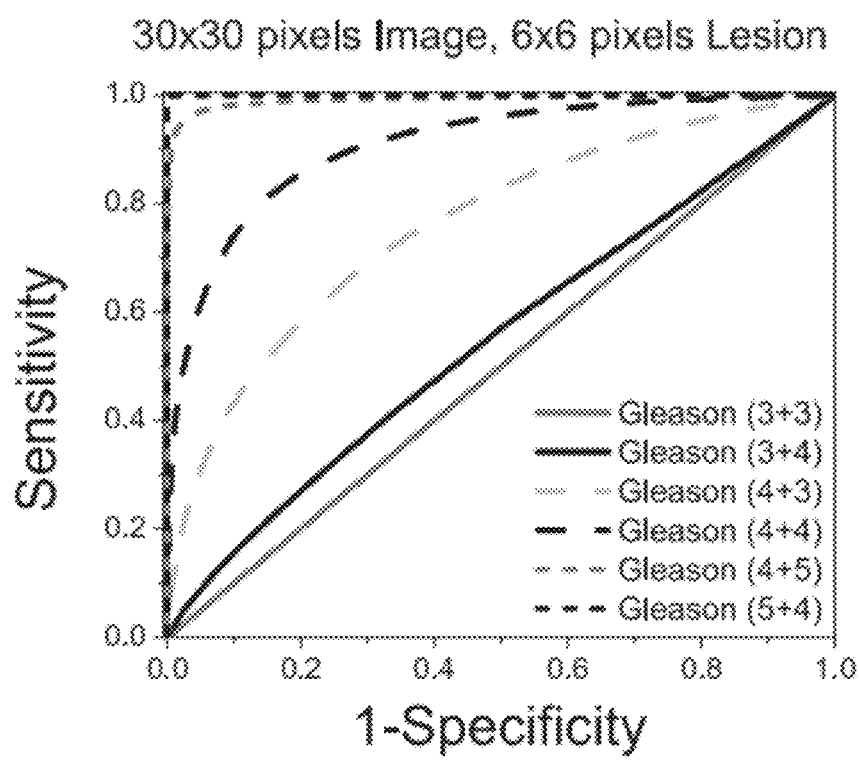

FIGS. 19A and 19B show ROC curves based on the analysis of maps representing 3×3 cm² prostate sections: FIG. 19A corresponds to 15×15 pixels maps incorporating 4×4 pixels cancer-lesions and FIG. 19B to 30×30 pixels maps incorporating 6×6 pixels cancer lesions. The respective tumour areas are 0.64 cm² and 0.36 cm², and their respective volumes (assuming a cubic shape) are 0.5 cm³ and 0.2 cm³. It will be noted that these values are beneath the diagnostic-relevant cancer-volume taken as references. FIGS. 19A and 19B clearly show that, in both configurations, for a fixed cancer-area the detection performance improves with the increase of Gleason grade. Furthermore, from FIGS. 19A and 19B it is clear that the pixel size/density plays an important role in the accuracy of detection: although FIG. 19B represents data from lesions of smaller area, i.e. 4% of total image area, the detectability is superior compared to the data depicted in FIG. 19A, where the simulated cancer area is around 7% of the total image. This is due to the denser sampling of the zinc distribution (4 times greater pixels per unit area).

Figure 20A:
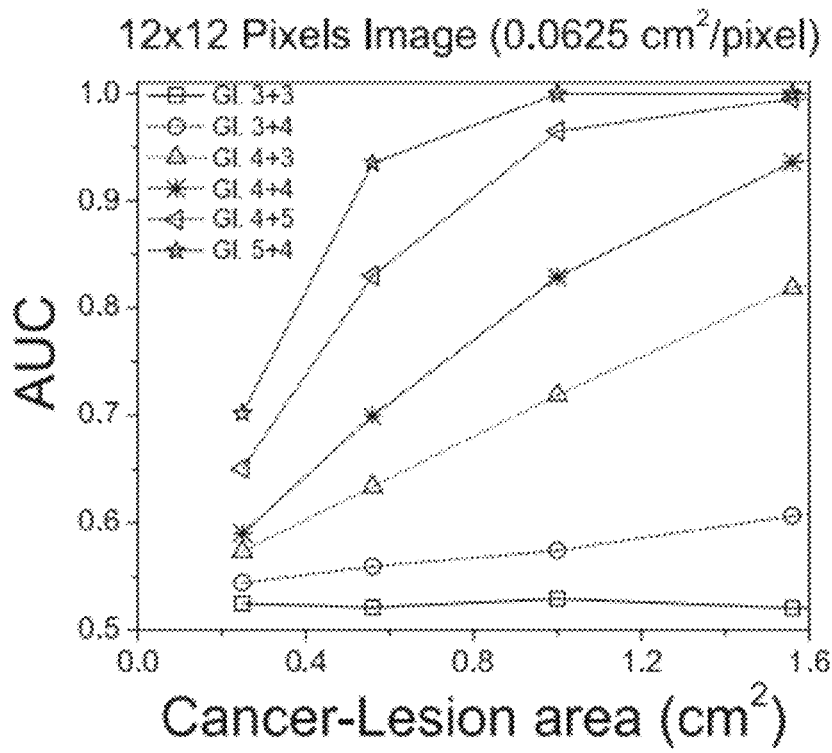
FIGS. 20A-20D show PCa detectability, expressed in terms of AUCs and plotted as function of the cancer-lesion dimension.
Figure 20B:
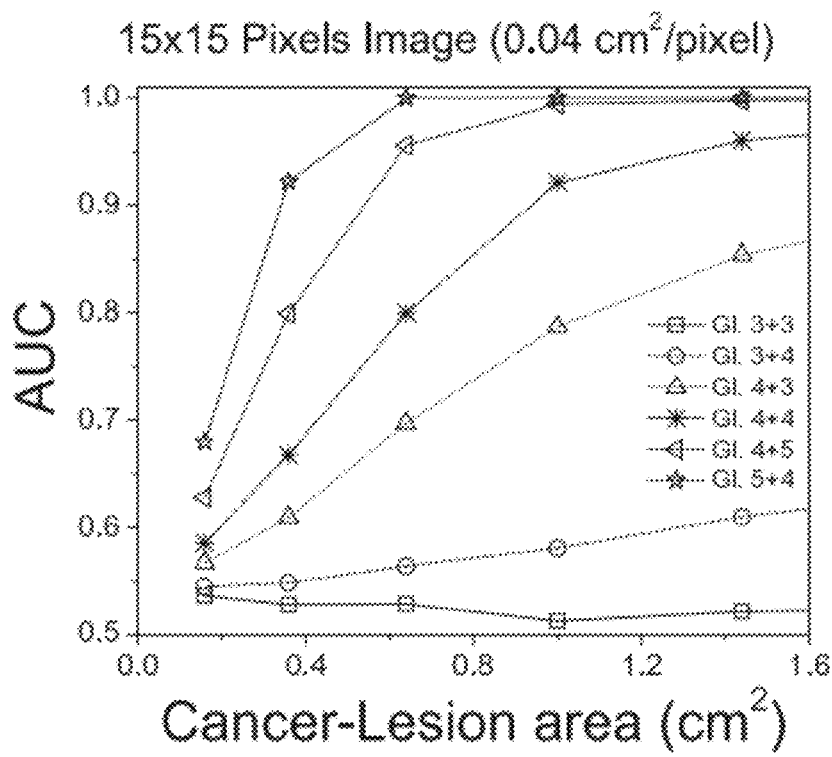
Figure 20C:
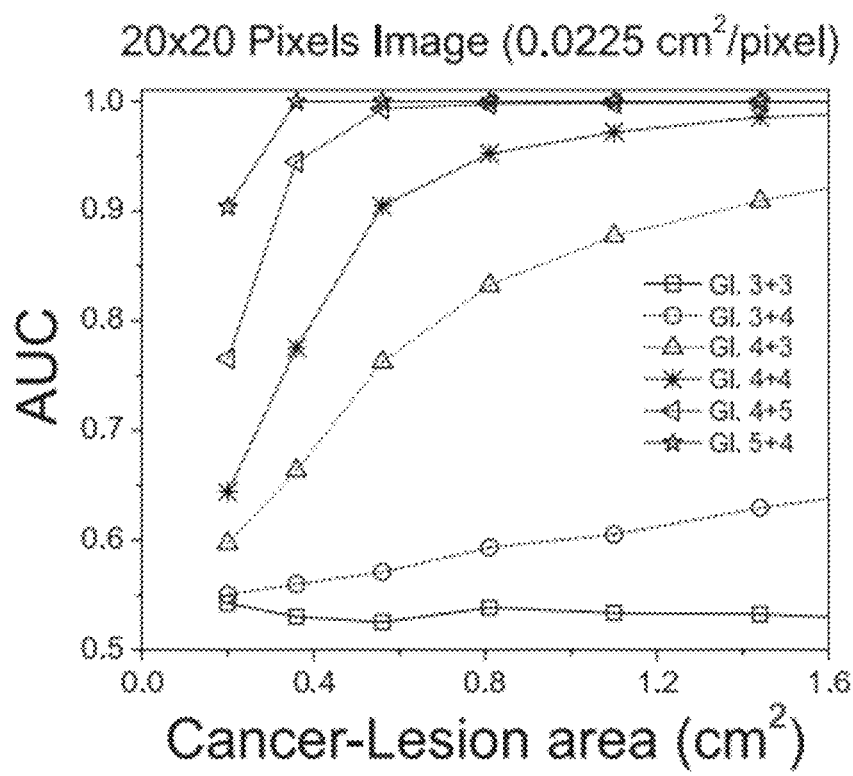
Figure 20D:
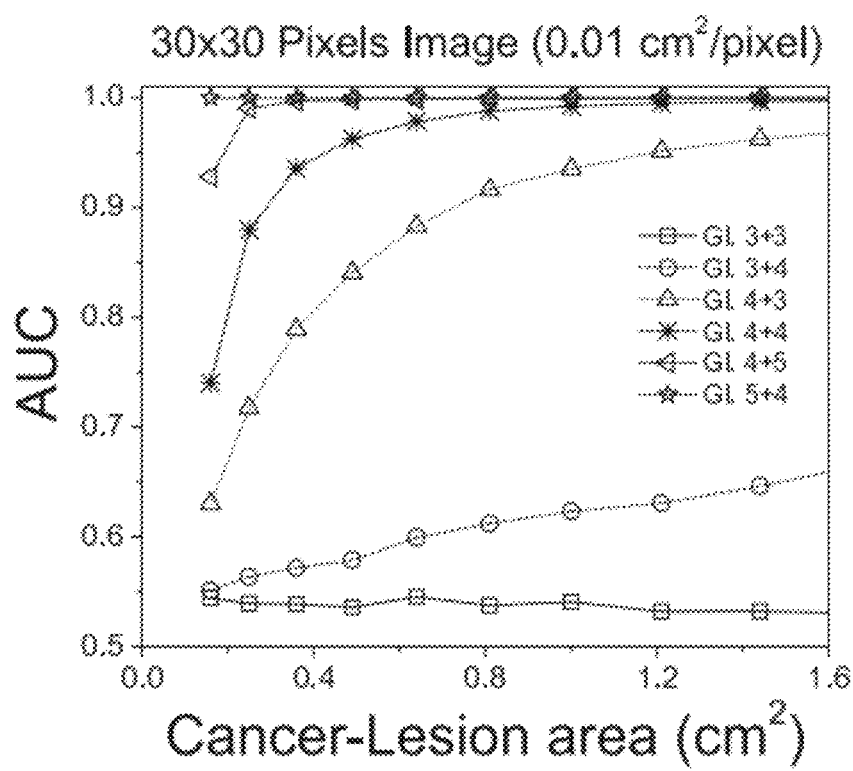

A systematic examination of the effect of pixel size/density is shown in FIGS. 20A-20D: the PCa detectability, expressed in terms of AUCs, is plotted as function of the cancer-lesion dimension. For each Gleason grade the ROC was computed for various spatial resolutions and cancer-lesion sizes. The 3×3 cm² area was divided into either 12×12, 15×15, 20×20 or 30×30 pixels images, with corresponding spatial resolutions of 0.0625, 0.04, 0.0225 or 0.01 cm² per pixel. The PCa detection performance is excellent in the case of high Gleason grade, even for very small lesion-size and relatively poor spatial resolution: for example, the detectability of the cancer-lesion (expressed in term of AUC) for high Gleason grade (5+4) is 100% (sensitivity=100%, specificity=100%) in the case of 30×30 pixels image, irrespective of the size of the lesion (FIG. 20D). On the contrary, low spatial resolution image, like 12×12 pixels image, reaches 100% of detectability only for cancer lesion area above the threshold of 1 cm², which represent a detection limit (FIG. 20A). Thus, this indicates that cancer area detection limit depends on both the zinc-map spatial resolution and the aggressiveness of the cancer (Gleason grade).

In general, the results of such simulations indicate that, under the present analysis scheme, there is an optimal spatial resolution for each lesion grade and size combination, and further improvement of the spatial resolution would not provide substantial improvement in terms of PCa detection. In order to achieve more efficient functional image processing for low Gleason grade lesions, perhaps an improved noise reduction process and a more effective image-segmentation algorithm could be employed.

The Effect of Tumour-Size on PCa Grading/Staging

The image processing scheme described in previous section, provides information on the location, size (number of pixels), average zinc levels and variance of the zinc distribution within each cluster. This information could be useful not only for detection and localization but also for grading and staging of the detected lesion. This is demonstrated in FIG. 21, which summarizes the relationship between $LC_{Zn}$ value and the detected cancer area, for various Gleason grades. The figure presents the average $LC_{Zn}$ and its standard deviation, versus the detected cancer area and its standard deviation, for different Gleason grades. The detected area is expressed as fraction of the entire zinc-map area. Each point in the figure was obtained from statistical analysis of a series of 500 computer-simulated 30×30 pixels images, in which a cancer lesion of certain area and random location was included. Each curve is the result of such analysis, with a series of increasing simulated lesion area, from 2×2 up to 11×11 pixels.

In the region below the "staging/grading limit" line, the curves in FIG. 21 (with the exception of Gleason grades 3+3 and 3+4, which are not distinguished, though separated from the higher grades) are separated by more than one standard deviation, thus affording unambiguous staging and grading of the detected lesion. Above this limit the results are ambiguous due to the overlap and the convergence of the curves to a single point (the "ambivalent point" in FIG. 21). The staging/grading limit line cuts the various curves at simulated (detected) lesion area values that are in turn dependent on the Gleason grade. For example, the value for Gleason grade (5+4) corresponds to a simulated (detected) lesion area threshold of less than 0.16 cm$^2$, or simulated (detected) lesion volume threshold of less than 0.064 cm$^3$. For a lower Gleason grade, of (4+3) for example, the value on FIG. 21 corresponds to a simulated (detected) lesion area threshold of ~0.5 cm$^2$ or simulated (detected) lesion volume threshold of 0.35 cm$^3$.

It will be noted that an actual detected cancer area will not be equal to the simulated one, but rather systematically larger, by a factor which depends on the Gleason grade. The accuracy of the area definition improves with increasing Gleason grade, due to the greater contrast between cancer and benign zinc distributions. For a practical application of this method, the information on the detected cancer-lesion area should be evaluated together with its zinc level (LC$_{Zn}$), in order to assess both the grade and the area. Then, for cancer volume above the threshold, the combination of the two could be used as an indication of the cancer-lesion location, size and grade.

In the case of low-grade cancers (3+3 and 3+4), the measured (FIG. 16) zinc concentration distributions are very similar to the non-PCa tissues; thus, their detection, based on the zinc-map and its analysis, is of low sensitivity and accuracy. These distributions can be measured with improved techniques, to determine whether better contrast with the benign background can be achieved, in order to adapt the present method for detection and localization of low-Gleason grade lesions.

Counting Statistics and PCa Detection Quality

Counting statistics is directly related to the radiation dose administered to the patient; clearly, the radiation dose should be kept at minimum.

The counting-statistics effects, which affect the image quality, are related to random fluctuations in the measured number of zinc XRF photons. In particular, the fluctuations degrade the precision of the image contrast, the information on the Lowest zinc value; this affects the tumour grading and the details of the lesion-edges and hence the information on the lesion dimensions. There is a trade-off between radiation-dose and image-quality; the optimization is important for the application of the zinc-based diagnostic approach.

In order to study and quantitatively estimate the effects of counting statistics that result from fluctuations in the XRF photon detection, we performed a Monte-Carlo study and ROC analysis; these consisted of 15×15 and 30×30 pixels images and two sets of 1000 images each, with and without cancer lesions. zinc-maps image were computer-simulated, using a first random number generator, as described herein. The maps were essentially pixel matrices whose elements represent zinc concentrations associated to specific locations within the map. Each pixel's content was then converted into number-of-counts, by multiplying the corresponding zinc-value by a specified sensitivity (counts per ppm per pixel). The effects of the sensitivity on cancer area detectability is schematically represented in FIG. 22. FIG. 22 shows that the better the sensitivity (Count/ppm/pixel), the more detailed the detected zinc distribution, and thus the more precise and detailed is the cancer area detection.

The number of counts per pixel was assumed to represent the mean value of a Poisson distribution. The final number of counts in that pixel was calculated by a second random-number generator based on Poissonian-sampling distribution with that mean; the pixel matrices resulting from this step were also processed following the procedure described herein. Examples of counting-statistics effects on processed images are shown in FIG. 23; starting from the same raw image (zinc-map image in the center), the same image processing may produce different diagnostic image results due to statistical fluctuation governed by Poissonian processes (see the four processed images in FIG. 23); this effect is especially evident for image processes involving low sensitivity.

Figure 24A:
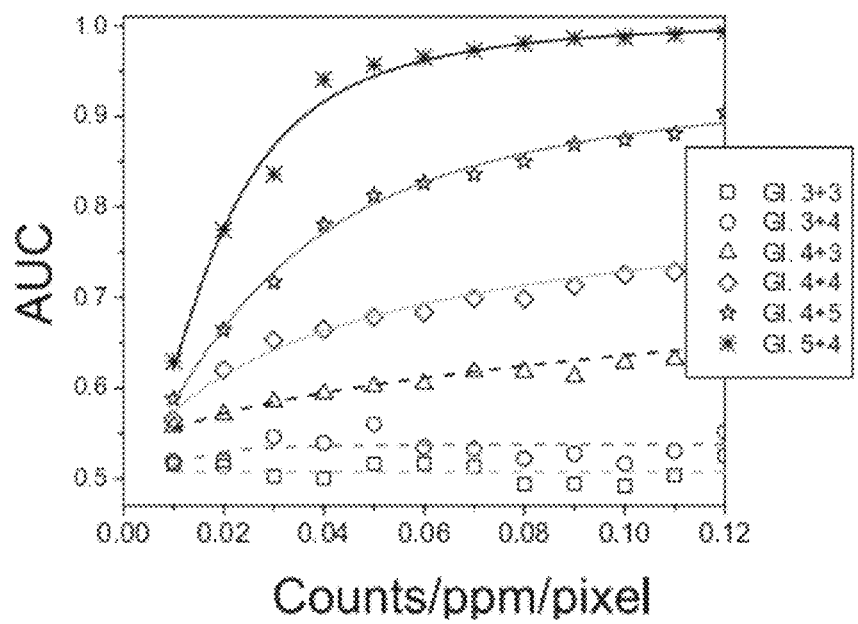
FIG. 24A illustrates the relationship between computed detectability and the sensitivity of the detection system, according to various exemplary embodiments of the present invention.
Figure 24B:
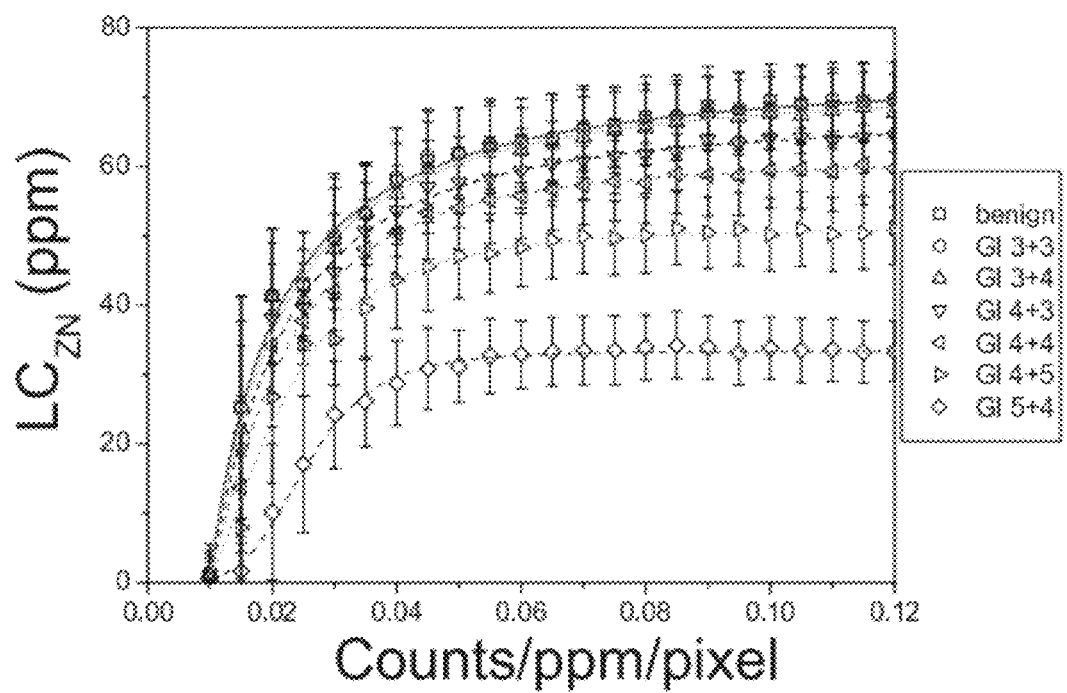
FIG. 24B depicts the correlation between grading classification and sensitivity, according to various exemplary embodiments of the present invention.

FIG. 24A illustrates the relationship between computed detectability and the sensitivity of the detection system: the AUCs values obtained by ROC analysis were used as a measure of the cancer-image detectability. FIG. 24B depicts the correlation between grading classification and sensitivity; cancer-lesion detection is based on Lowest zinc value (LC$_{Zn}$) measured after noise reduction and image segmentation. The analysis encompasses 15×15 pixels zinc-map images with 4×4 pixels lesions (occupying 7% of the image area).

As can be seen from FIGS. 24A and 24B, the overall effect of counting statistics on lesion-area detectability depends, non-linearly, on the total number of detected counts per unit concentration of zinc. As the counting statistics improve, the detectability and LC$_{Zn}$ asymptotically converge to values which depend solely on the intrinsic contrast of zinc level between the surrounding benign tissue (on the Gleason grade of the cancer lesion) and the analyzed tissue voxel. At the point of convergence, the counting-statistics no longer affect the results. In addition, it follows that, above an intrinsic instrumental sensitivity of ~0.1 counts/ppm/pixel, the counting statistics do not play a significant role, neither on the detectability nor on the histological classification of the detected cancer-lesion. This result is not dependent on the image's spatial resolution; therefore, this points at an optimal irradiation dose, with no diagnostic advantage for higher doses of radiation.

Taken together, the results of the simulations described herein indicate that an inclusive image of the histological-grading probability for the examined prostatic tissue could be of a prime importance for the decision-making process of needle-biopsy site selection.

Based on the relationship between total number of pixels (image spatial resolution), lesion-size, cancer aggressiveness (Gleason grade) and counting statistics, an exceptional sensitivity in detecting small PCa lesions, even with rough spatial resolution, could be reached for aggressive cancer lesions (Gleason grade 4+3 and above). The results indicate that the analysis of the zinc maps may provide important knowledge concerning the geometry of lesions encountered in a clinical setting, and the degree of confidence in the prognostic results as function of some system parameters such as spatial resolution and sensitivity. zinc frequency distributions for low-grade cancer lesions (primary Gleason grade 3) were similar to those of non-cancerous tissue, and are in need of possible further processing in order to provide valuable results. However, since the input zinc frequency distributions, as shown in FIG. 16, are average ones, and based on data obtained from several PCa patients in each Gleason grade category, without consideration of patient-to-patient variation in the zinc metabolism, there is a possibility that the zinc distributions in patients with lower Gleason grades (e.g. 3+3 and 3+4) could be narrower than the ones shown in FIG. 16 and thus could provide better differentiation from the signals from non-cancerous tissue. In such a case, more accurate diagnostic values are expected from the zinc-map method—even for the low-grade cases.

Regarding counting statistics, the results disclosed herein show that the overall effect of counting statistics on cancer-lesion area detectability depends, from a qualitative point of view, on multiple factors such as image spatial resolution, intrinsic instrumental sensitivity and total irradiation time (dose) per pixel. The detectability of the cancer-lesion area is directly proportional to the zinc-image contrast, which in turn depends on the histological grade of the detected cancer (lower zinc concentration for higher Gleason grade). To some extent, high-spatial resolution increases detectability and, at the expense of an increase of the noise level (low statistics), it permits detecting smaller tumours.

The design of a zinc-mapping instrument can be based on a compromise between dose consideration, total irradiation time and patient comfort, counting statistics effects and instrumental sensitivity of the detection system. The present Monte-Carlo study provides invaluable information on the significance of each variable to the overall diagnostic potential.

The proposed zinc-based mapping method is expected to have significant impact on early diagnosis of prostate cancer. zinc mapping, being a non-invasive examination, can be employed as an additional screening tool, prior to referring the patient to needle biopsy, can improve the distinction between benign and malignant conditions (e.g. BPH vs PCa), provide grading and geometrical information concerning cancer-lesion, thus refining the process of patient selection for biopsy. This can, in turn, reduce the number of unnecessary biopsy procedures performed increase the cost effectiveness of needle biopsy examination. It will thus facilitate extension of the biopsy examination to younger persons with PSA lower than 4 ng/ml, offering an improved screening strategy, and can thus have considerable impact on the life quality and expectancy of prostate-cancer patients.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

What is claimed is:

1. A method of analyzing a plurality of biopsy cores extracted from a plurality of respective biopsy locations in a prostate, the analysis being for determining a future biopsy location in the prostate, the method comprising:
    measuring a level of zinc in each of said biopsy cores;
    associating to each biopsy location at least one zinc level measured from a respective core, thereby generating a zinc map of at least a portion of the prostate based on said levels and said respective biopsy locations;
    calculating a gradient of zinc level over said zinc map; and
    using said gradient for determining at least one additional biopsy location for a future biopsy in the prostate.

2. A method of guiding a biopsy device in a prostate, comprising:
    extracting a plurality of biopsy cores from a plurality of respective biopsy locations in the prostate;
    measuring a level of zinc in each of said biopsy cores;
    associating to each biopsy location at least one zinc level measured from a respective core, thereby generating a zinc map of at least a portion of the prostate based on said levels and said respective biopsy locations;
    calculating a gradient of zinc level over said zinc map;
    using said gradient for determining at least one additional biopsy location for a future biopsy in the prostate; and
    guiding a biopsy device to said at least one additional biopsy location, and extracting at least one biopsy core from said at least one additional biopsy location.

3. The method according to claim 1, further comprising adding to the plurality of biopsy cores at least one additional biopsy core from the prostate at said at least one additional biopsy location, thereby updating the plurality of biopsy cores, measuring a level of zinc in said at least one additional biopsy core to provide at least one additional zinc level, updating said zinc map based on said at least one additional zinc level, and repeating said determination for said updated map.

4. The method according to claim 1, further comprising displaying at least one of: said plurality of respective biopsy locations, said zinc map, and said at least one additional biopsy location on an image of the prostate.

5. The method according to claim 1, further comprising estimating a location of a tumor in the prostate.

6. The method of claim 5, further comprising estimating a size of said tumor.

7. The method according to claim 5, wherein said at least one additional biopsy location comprises a plurality of additional biopsy locations at said tumor.

8. The method according to claim 5, wherein said at least one additional biopsy location comprises at least one additional biopsy location nearby said tumor.

9. The method according to claim 1, further comprising removing the biopsy cores from biopsy devices to a core holder prior to said measurement, wherein said removal is done automatically.

10. The method according to claim 1 further comprising estimating a grade of a prostate cancer from said zinc map.

11. The method of claim 1, further comprising measuring a distribution of said zinc along each core, wherein said generating said zinc map is based on said distribution.

12. The method of claim 2, further comprising measuring a distribution of said zinc along each core, wherein said generating said zinc map is based on said distribution.

* * * * *